(12) United States Patent
Chilkoti et al.

(10) Patent No.: US 8,497,356 B2
(45) Date of Patent: Jul. 30, 2013

(54) BIOMOLECULE POLYMER CONJUGATES AND METHODS FOR MAKING THE SAME

(75) Inventors: Ashutosh Chilkoti, Durham, NC (US); Weiping Gao, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/201,502

(22) PCT Filed: Feb. 17, 2010

(86) PCT No.: PCT/US2010/024385
§ 371 (c)(1),
(2), (4) Date: Aug. 15, 2011

(87) PCT Pub. No.: WO2010/096422
PCT Pub. Date: Aug. 26, 2010

(65) Prior Publication Data
US 2011/0294189 A1    Dec. 1, 2011

Related U.S. Application Data

(60) Provisional application No. 61/153,167, filed on Feb. 17, 2009.

(51) Int. Cl.
*C07K 1/00* (2006.01)
(52) U.S. Cl.
USPC .......................................... 530/402; 530/350
(58) Field of Classification Search
None
See application file for complete search history.

(56) References Cited

U.S. PATENT DOCUMENTS

| | | | |
|---|---|---|---|
| 6,207,749 B1 | 3/2001 | Mayes et al. | |
| 6,623,950 B1 | 9/2003 | von der Osten et al. | |
| 2006/0034796 A1 | 2/2006 | Ashwell et al. | |
| 2007/0087114 A1 | 4/2007 | Chilkoti et al. | |
| 2008/0181861 A1 | 7/2008 | Jiang et al. | |

OTHER PUBLICATIONS

Lele et al., "Synthesis of Uniform Protein-Polymer Conjugates", Biomacromolecules 2005, 6, 3380-3387.*
Grover et al., "Protein-Polymer Conjugates: Synthetic Approaches by Controlled Radical Polymerizations & Interesting Applications", Curr Opin Chem Biol., Dec. 2010 ; 14(6): 818-827.*
Drucker et al., "The incretin system: glucagon-like peptide-1 receptor agonists and dipeptidyl peptidase-4 inhibitors in type 2 diabetes" Lancet, 2006, 368: 1696-1705.
Gao, W., et al., "In situ growth of a PEG-like polymer from the C terminus of an intein fusion protein improves pharmacokinetics and tumor accumulation" PNA Early Edition, 2010, 1-6.
Ge et al., "Self-Cleavable Stimulus Responsive Tags for Protein Purification without Chromatography" J. Am. Chem. Soc., 2005, 127: 11228-11229.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin., 2003, 31(3): 529-540.
Hassouneh, W., et al., "Elastin-like Polypeptides as a Purification Tag for Recombinant Proteins" Curr Protoc Protein Sci. Aug. 2010 ; Chapter: Unit-6.11, (20 pages).
Knudsen, "Glucagon-like Peptide-1: The Basis of a New Class of Treatment for Type 2 Diabetes" J. Med. Chem, 2004, 47: 4128-4134.
Lele, B., et al., "Synthesis of Uniform Protein-Polymer Conjugates" Biomacromolecules 2005, 6, 3380-3387.
Lim, et al., "Improved Non-Chromatographic Purification of a Recombinant Protein by Cationic Elastin-like Polypeptides" Biomacromolecules, 2007, 8(5): 1417-1424.
McHale et al., "Synthesis and in Vitro Evaluation of Enzymatically Cross-Linked Elastin-Like Polypeptide Gels for Cartilaginous Tissue Repair" Tissue Engineering, 2005, 11: 1768-1779.
Pace et al., "How to measure and predict the molar absorption coefficient of a protein" Protein Science 1995, 4: 2411-2423.
Trabbic-Carlson, K., "Expression and purification of recombinant proteins from *Escherichia coli*: Comparison of an elastin-like polypeptide fusion with an oligohistidine fusion" Protein Science, 2004, 13: 3274-3284.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
PCT/US2010/024385 International Preliminary Report on Patentability and Written Opinion dated May 5, 2010 (7 pages).
PCT/US2010/024385 International Search Report dated May 5, 2010 (2 pages).

* cited by examiner

*Primary Examiner* — Suzanne M Noakes
(74) *Attorney, Agent, or Firm* — Michael Best & Friedrich LLP

(57) ABSTRACT

Methods for producing biomolecule-polymer conjugates, such as polypeptide-polymer conjugates, include attachment of an initiator agent to a biomolecule and in situ polymerization of a polymer from defined sites on the biomolecule. The conjugates may have desirable pharmacological properties and may be used therapeutically.

12 Claims, 37 Drawing Sheets

Monomer structures for ATRP and RAFT polymerization

R:

Or R may be alkyl such as methyl, ethyl, propyl and isopropyl, and benzyl,
Betaine such as carboxybetaine, sulfobetaine,
Oligoethylene glycol (OEG) or polyethyleneglycol (PEG)

R: may be Alkyl such as methyl, ethyl, propyl and isopropyl, and benzyl,
Betaine such as carboxybetaine, sulfobetaine,
Oligoethylene glycol (OEG) or polyethyleneglycol (PEG)

BIOMOLECULE POLYMER CONJUGATES AND METHODS FOR MAKING THE SAME

CROSS REFERENCE TO RELATED APPLICATIONS

This application is a national stage filing under 35 U.S.C. 371 of International Application No. PCT/US2010/024385, filed on Feb. 17, 2010, which claims the benefit of priority to U.S. Provisional Application No. 61/153,167, filed on Feb. 17, 2009, the disclosures of which are herein incorporated by reference in their entireties for any purpose.

BACKGROUND

Proteins and other biomolecules may be used for a number of diagnostic, monitoring and treatment applications by virtue of having high biological activity and specificity. However, the delivery of biomolecules such as therapeutic proteins, oligonucleotides or other pharmaceutical agents in their unmodified forms may have several limitations which include poor stability, low solubility, short circulating half-lives and immunogenic potential. Frequent administration of the agent may be required, which may increase cost, inconvenience and the risk of adverse reactions.

SUMMARY

Methods are provided of increasing the half-life of biomolecules, such as polypeptides, by forming conjugates containing a polymer and a biomolecule or polypeptide. In one aspect, the methods may increase the half life of a plurality of polypeptides having N-termini and C-termini. In some embodiments, the polypeptides are contacted with an initiator agent under conditions that permit attachment of the initiator agent to at least one of the N-terminus and the C-terminus of the polypeptides, and are incubated with a monomer under conditions that permit polymerization to occur from the initiator agent to form polypeptide-polymer conjugates. In some embodiments, polymerization may occur such that at least about 10% of the polypeptides have a conjugated polymer initiated from at least one of the N-terminus and the C-terminus, and the polypeptide-polymer conjugates have an in vivo half-life that is at least 50% greater than the in vivo half-life of the polypeptides.

Methods are also provided of increasing the half life of a biomolecule by contacting the biomolecule with an initiator agent under conditions that permit attachment of the initiator agent to the biomolecule. The biomolecule may be incubated with a monomer under conditions that permit polymerization to occur from the initiator agent to form a biomolecule-polymer conjugate, and the biomolecule-polymer conjugate may have an in vivo half-life that is at least 50% greater than the in vivo half-life of the biomolecule.

Other aspects of the invention will become apparent by consideration of the detailed description and accompanying drawings.

GFP-Br: $R_h$=3.1 nm, Polydispersity=21.3%, regularization fit. GFP-C-poly(OEGMA):$R_h$=22 nm, Polydispersity=21.1%, regularization fit.

Figure 31:
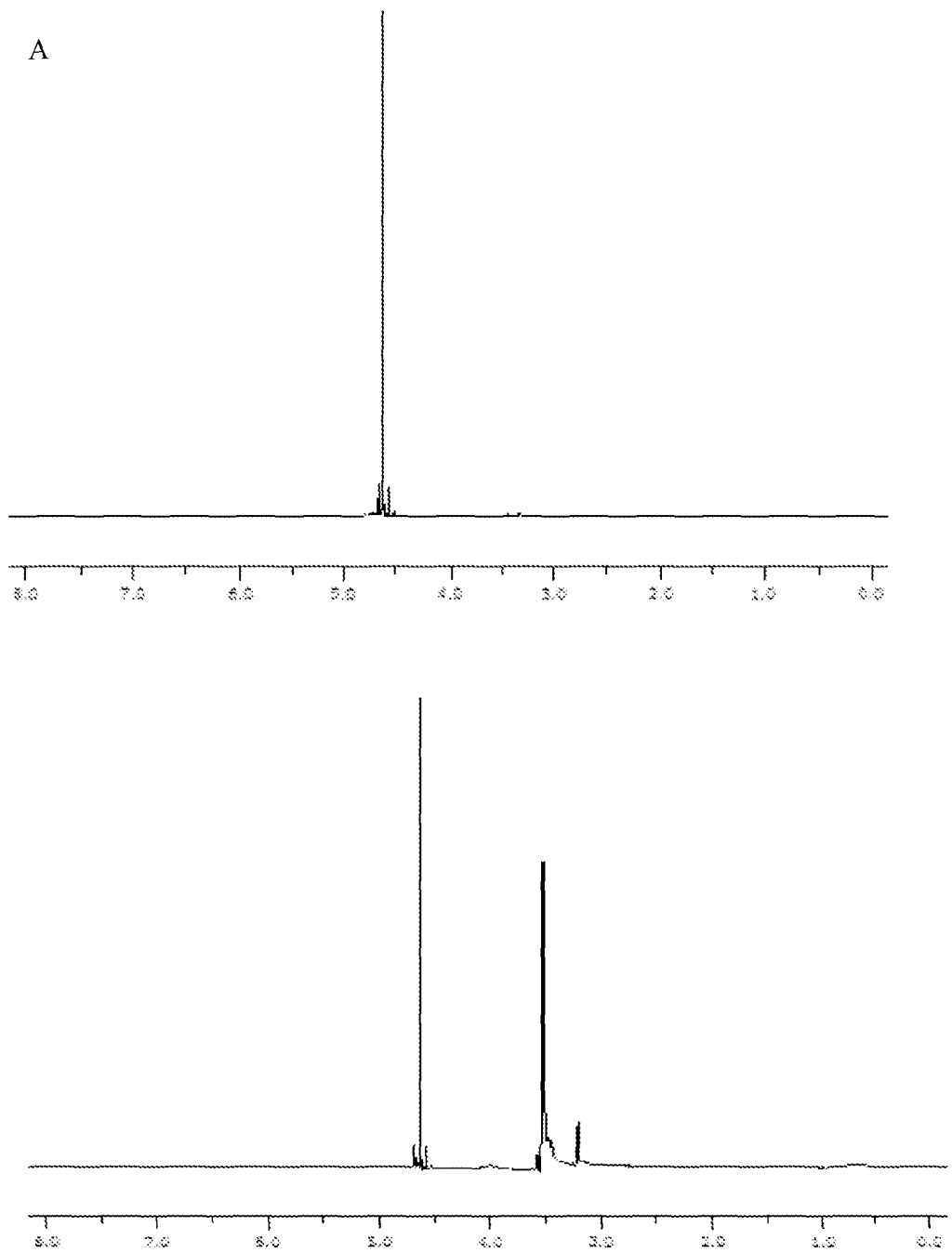

FIG. 31: Graph showing $^1$H NMR spectra of: (A) GFP-Br, and (B) GFP-C-poly(OEGMA) in deuterated water FIG. 32: Graph showing UV/Vis spectra of GFP-SO3H (a), GFP-Br (b) and GFP-C-poly(OEGMA) (c) at the same concentration of 1 μM in phosphate buffer solution.

Figure 33:
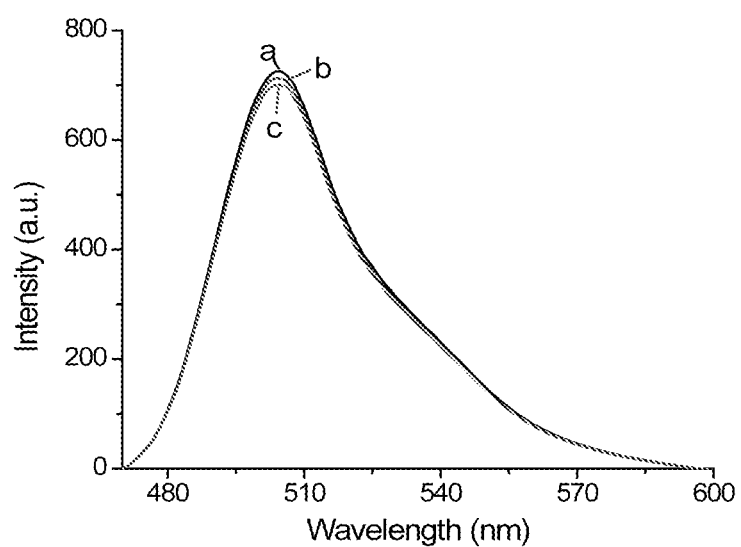

FIG. 33: Graph showing fluorescence spectra of GFP-SO3H (a), GFP-Br (b) and GFP-C-poly(OEGMA) (c) at a concentration of 1 μM in phosphate buffer at an excitation wavelength of 460 nm.

Figure 34:
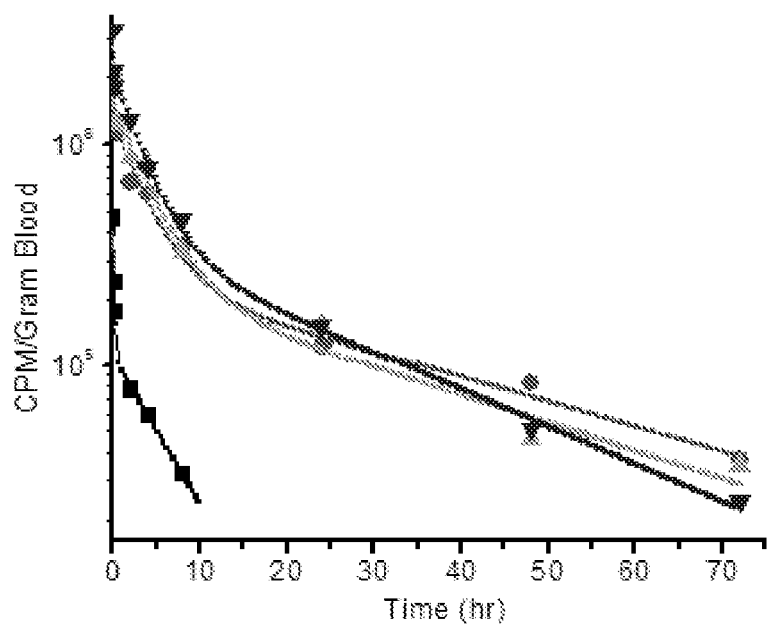

FIG. 34: Graph showing blood concentration as a function of time post-injection. GFP: square; GFP-C-poly(OEGMA) (D=26, 42, 80 nm): sphere, triangle and upside down triangle symbols, respectively.

Figure 35:
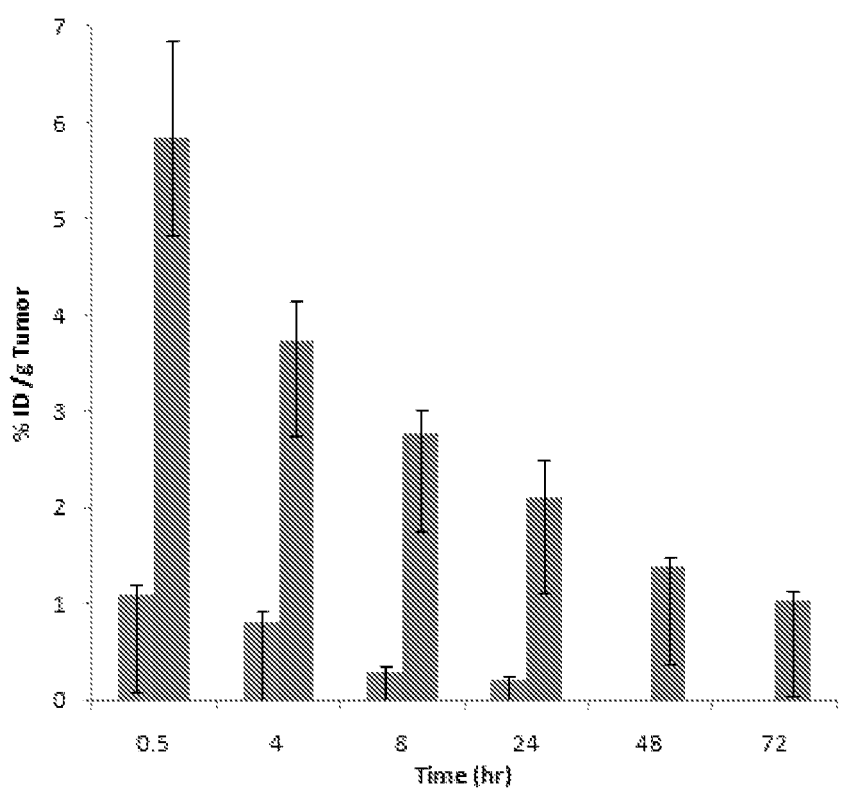

FIG. 35: Graph showing biodistribution as a function of time post-injection. GFP: Left column; GFP-C-poly (OEGMA) (D=42 nm): Right column.

Figure 36:
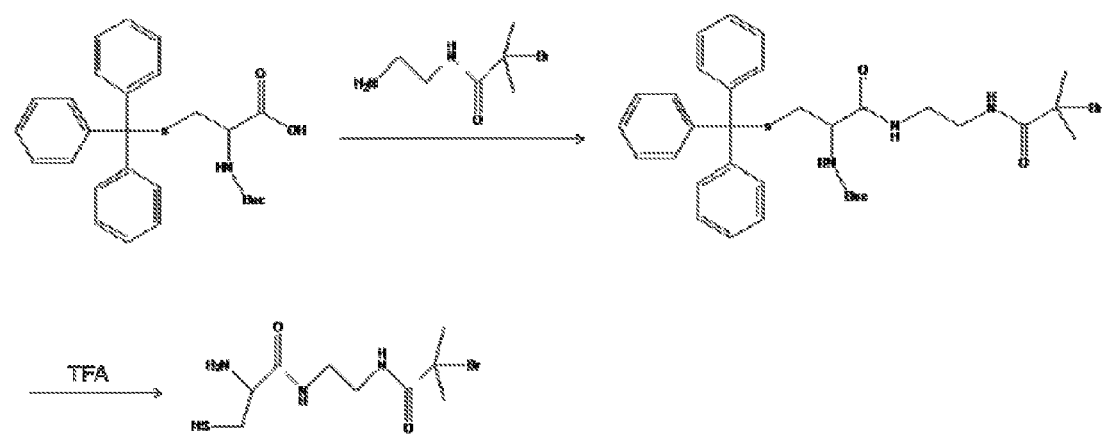

FIG. 36: Schematic illustration showing synthesis of a cysteine-functionalized ATRP initiator.

Figure 37:
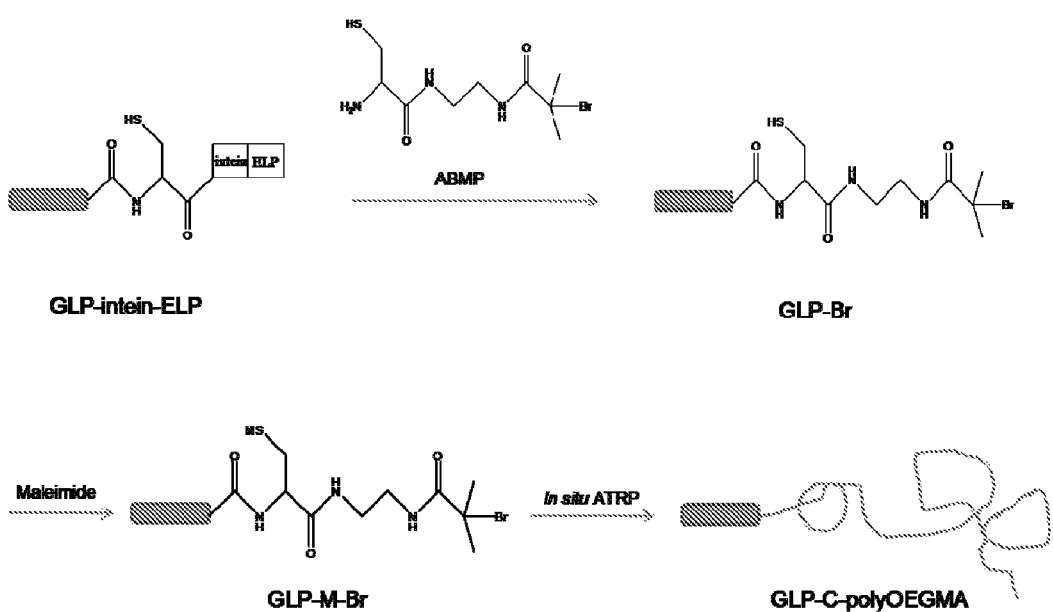

FIG. 37: Schematic illustration showing synthetic route of GLP-C-poly(OEGMA) conjugates.

DETAILED DESCRIPTION

Biomolecule-polymer conjugates may be formed by attaching preformed polymers with reactive end groups to targets on the biomolecules via a variety of coupling reactions. For example, conjugation of therapeutic proteins with polymers such as polyethylene glycol, can prolong the serum half-life and reduce immunogenicity of the proteins. However, the stability and properties of these conjugates may be insufficient and difficult to predict, because the type and frequency of attachment of the preformed polymer may be difficult to control.

Methods are provided for synthesizing biomolecule-polymer conjugates, in which the polymer is formed in situ on the biomolecule, such as at the end of the biomolecule, or at specified sites along the sequence of the biomolecule. Examples of biomolecules include but are not limited to, peptides, polypeptides, proteins, oligonucleotides, polynucleotides or aptamers. In one embodiment, the biomolecule is a polypeptide. The biomolecule-polymer conjugates show an increased half-life in vivo or in serum, or other desirable pharmacological properties, compared with biomolecules that have not had polymers formed in situ according to methods described herein. The methods facilitate deposition and growth of polymers that can be regulated and controlled to produce a conjugate having particular desired features.

Methods for synthesizing polypeptide-polymer conjugates are also provided in which a polymer is synthesized in situ from an N-terminus or C-terminus of the polypeptide. The N- or C-terminus of the polypeptide, for example, is modified with an initiator agent that facilitates polymerization from the N- or C-terminus. Polymers may also be synthesized in situ from the 5' or 3' ends of polynucleotides.

The biomolecule-polymer conjugates comprise a biomolecule to which a polymer is attached at one or more ends of the biomolecule, or at specified sites within the biomolecule, or a combination thereof. In one embodiment, the biomolecule is a polypeptide. Examples of polypeptides include, but are not limited to, proteins, polypeptides, and peptide sequences. Examples of proteins and polypeptides include any natural or synthetic polypeptide that may be administered to a patient. In one embodiment the biomolecule is a polynucleotide.

Examples of polypeptides include, but are not limited to, those of interest in medicine, agriculture and other scientific and industrial fields, particularly including therapeutic polypeptides such as inteferons, insulin, monoclonal antibodies, blood factors, colony stimulating factors, growth hormones, interleukins, growth factors, therapeutic vaccines, calcitonins, tumor necrosis factors (TNF), and enzymes. Specific examples of such therapeutic proteins include, without limitation, enzymes utilized in enzyme replacement therapy; hormones for promoting growth in animals, or cell growth in cell culture; anticoagulants and active proteinaceous substances used in various applications, for example, in biotechnology or in medical diagnostics. Specific examples include, but are not limited to: asparaginase; glutamase; arginase; arginine deaminase; adenosine deaminase ribonuclease; cytosine deaminase, trypsin; chymotrypsin, papin, epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; luteinizing hormone-releasing hormone (LHRH); growth hormone-releasing hormone (GHRH); tissue plasminogen activators; interleukin-1; interleukin-15; receptor antagonist (IL-1RA); glucagon-like peptide-1 (GLP-1); leptin, ghrelin; granulocyte monocyte colony stimulating factor (GM-CSF); interleukin-2 (IL-2); interferons such as interferon-$\alpha$; adenosine deaminase; uricase; asparaginase; human growth hormone; asparaginase; macrophage activator; chorionic gonadotropin; heparin; atrial natriuretic peptide; hemoglobin; retroviral vectors; relaxin; cyclosporin; oxytocin; vaccines; monoclonal antibodies; single chain antibodies, ankyrin repeat proteins, affibodies, and the like; and analogs and derivatives thereof.

Examples of polynucleotides include, but are not limited to, polynucleotides and oligonucleotide sequences, including DNA and RNA, which may be double-stranded or single-stranded. Examples of polynucleotides include any natural or synthetic polynucleotide that may be administered to a patient. Examples of polynucleotides include, but are not limited to, antisense oligonucleotides, silencing RNA (siRNAs), anti-microRNA (anti-miR) that target genes such as bcl-2, V2R, EphA2, caveolin-1, TNF-alpha, MIF, GFP, Raf-1, c-raf, luciferase, VEGF, SCV, Fas, Ins2, Caspase-8, and HBsAg.

Examples of aptamers include, but are not limited to, vascular endothelial growth factor (VEGF) aptamer, Ricin aptamer, pepocin aptamer, gypsphilin aptamer, thrombin aptamer, activated plasma protein C aptamer, HIV-1 reverse transcriptase, HIV-1 integrase, protein kinase C aptamer, human neutrophil elastase aptamer, L-selectin aptamer, P-selectin aptamer, *Yersinia* protein tyrosine phosphatase aptamer, phospholipase A2, angiogenin aptamer, and rhinovirus capsid protein aptamer.

Other examples of biomolecules include, but are not limited to, oxytocin, vasopressin, adrenocorticotrophic hormone, prolactin, luliberin or luteinising hormone releasing hormone, growth hormone, growth hormone releasing factor, somatostatin, glucagon, gastrin, tetragastrin, pentagastrin, urogastroine, secretin, calcitonin, enkephalins, endorphins, angiotensins, renin, bradykinin, bacitracins, polymixins, colistins, tyrocidin, gramicidin's, and synthetic analogues, modifications and pharmacologically active fragments thereof, monoclonal antibodies and soluble vaccines.

The polymer that is grown in situ from the biomolecule confers desirable properties to the conjugate. The term "polymer" as used herein is intended to encompass a homopolymer, heteropolymer, block polymer, co-polymer, ter-polymer, etc., and blends, combinations and mixtures thereof. Examples of polymers include, but are not limited to, functionalized polymers, such as a polymer comprising 5-vinyltetrazole monomer units and having a molecular weight distribution less than 2.0. The polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Such a block copolymer may further be capable of selective separation of closely related chemical species such as ions, proteins or nucleic acids via ionic bonding or complex formation.

Polymers that can be produced in situ on the biomolecule or polypeptide according to the methods disclosed herein include, without limitation, polyesters, poly(meth)acrylamides, poly(meth)acrylates, polyethers, polystyrenes, and polynorbornenes. For example, amphiphilic comb polymers are described in U.S. Patent Application Publication No. 2007/0087114 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other polymers include, but are not limited to, polyalkylenes such as polyethylene and polypropylene; polychloroprene; polyvinyl ethers; such as poly(vinyl acetate); polyvinyl halides such as poly(vinyl chloride); polysiloxanes; polystyrenes; polyurethanes; polyacrylates; such as poly(methyl (meth)acrylate), poly(ethyl (meth)acrylate), poly(n-butyl(meth)acrylate), poly(isobutyl (meth)acrylate), poly(tert-butyl (meth)acrylate), poly(hexyl(meth)acrylate), poly(isodecyl (meth)acrylate), poly(lauryl (meth)acrylate), poly(phenyl (meth)acrylate), poly(methyl acrylate), poly (isopropyl acrylate), poly(isobutyl acrylate), and poly(octadecyl acrylate); polyacrylamides such as poly(acrylamide), poly(methacrylamide), poly(ethyl acrylamide), poly(ethyl methacrylamide), poly(N-isopropyl acrylamide), poly(m, iso, and tert-butyl acrylamide); and copolymers and mixtures thereof. These polymers may include useful derivatives, including polymers having substitutions, additions of chemical groups, for example, alkyl groups, alkylene groups, hydroxylations, oxidations, and other modifications routinely made by those skilled in the art. The polymers may have side chains of betaine, carboxybetaine, sulfobetaine, oligoethylene glycol (OEG) or polyethyleneglycol (PEG). For example, poly(OEGMA) may be used in methods of the invention to produce polypeptide-p-OEGMA or biomolecule-poly(OEGMA) conjugates. Poly(OEGMA) may be hydrophilic, water-soluble, non-fouling, non-toxic and non-immunogenic due to the OEG side chains, such that conjugating proteins or polypeptides at the N- and/or C-termini with poly(OEGMA) can improve protein stability, pharmacokinetics and immunogenicity.

The biomolecule-polymer conjugates may be formed by contacting the biomolecule with an initiator and one or more monomers under conditions that permit polymerization to occur. In one embodiment, the biomolecule is a polypeptide. To form the polymer in situ and produce a conjugate, the biomolecule may be contacted with an initiator agent under conditions that permit attachment of the initiator agent to the biomolecule. The initiator attaches to the biomolecule, for example to the end of the biomolecule, such as at one or more of the N-terminus or C-terminus of a polypeptide, protein or combination thereof, or such as at one or more of the 5' or 3' end of a polynucleotide. The biomolecule and initiator may be contacted subsequently or at least partially simultaneously with a monomer under conditions suitable for polymerization to occur. Accordingly, initiation sites on the biomolecule can be generated prior to polymerization, or concurrently as polymerization occurs. Polymerization may include, for example, atom transfer radical polymerization (ATRP), reversible addition-fragmentation chain transfer (RAFT) polymerization, ring-opening metathesis polymerization (ROMP), and combinations thereof.

The methods may permit precise design of biomolecule-polymer conjugates, polypeptide-polymer conjugates, or protein-polymer conjugates and may provide advantages that include a reduction or elimination of postpolymerization modification strategies and biomolecule-polymer, polypeptide-polymer, or protein-polymer coupling reactions, and simplification of the purification of the final bioconjugate from monomer, polymer and/or catalyst. The methods may permit attachment of polymers to biomolecules in a sample such that at least about 10%, at least about 20%, at least about 30%, at least about 40%, at least about 50%, at least about 60%, at least about 70%, at least about 80%, at least about 90%, or at least about 95% of the polypeptides or biomolecules in the sample have one polymer attached per biomolecule. Stoichiometric attachment of one, two, three, four, five, six, seven, eight, nine, or ten or more polymers per biomolecule such that at least about 10%, at least about 20%, at least about 30%, at least about 40%, at least about 50%, at least about 60%, at least about 70%, at least about 80%, at least about 90%, or at least about 95% of biomolecules in the sample have the particular desired number of polymers attached is also permitted.

The methods may permit attachment of polymers to biomolecules in a sample such at least about 10%, at least about 20%, at least about 30%, at least about 40%, at least about 50%, at least about 60%, at least about 70%, at least about 80%, at least about 90%, or at least about 95% of the biomoleules have a conjugated polymer initiated from at least one end of the biomolecule, such as the 5' or 3' end of a polynucleotide. The biomolecule-polymer conjugates may be substantially free of attachment of polymers at sites within the biomolecule. The polypeptide-polymer conjugates may be substantially free of attachment of biomolecules throughout the polymers.

For example, the methods may permit attachment of polymers to polypeptides in a sample such at least about 10%, at least about 20%, at least about 30%, at least about 40%, at least about 50%, at least about 60%, at least about 70%, at least about 80%, at least about 90%, or at least about 95% of the polypeptides have a polymer attached to the N-terminus, the C-terminus or both the N and C-termini. The polypeptide-polymer conjugates may be substantially free of attachment of polymers at sites within the polypeptide. The polypeptide-polymer conjugates may be substantially free of attachment of polypeptides throughout the polymers.

Figure 1:
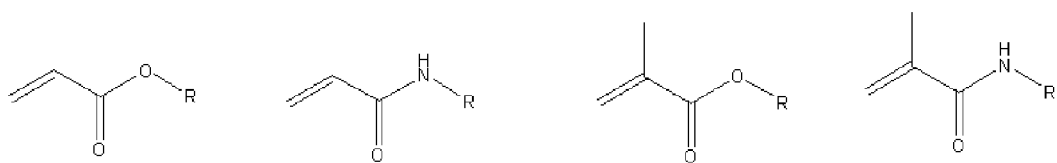
FIG. 1: Diagram showing monomer structures for use with ATRP and RAFT polymerization.
Figure 1:
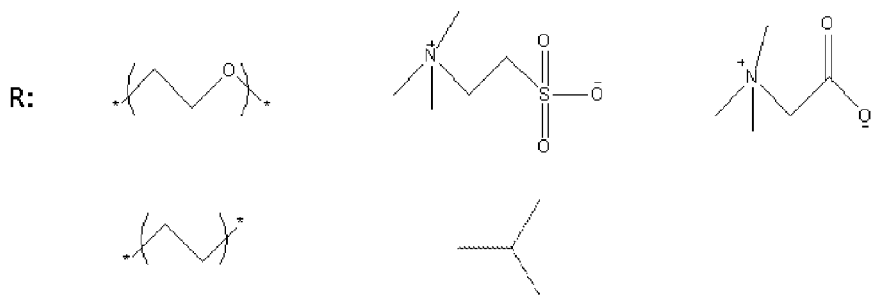
Figure 2:
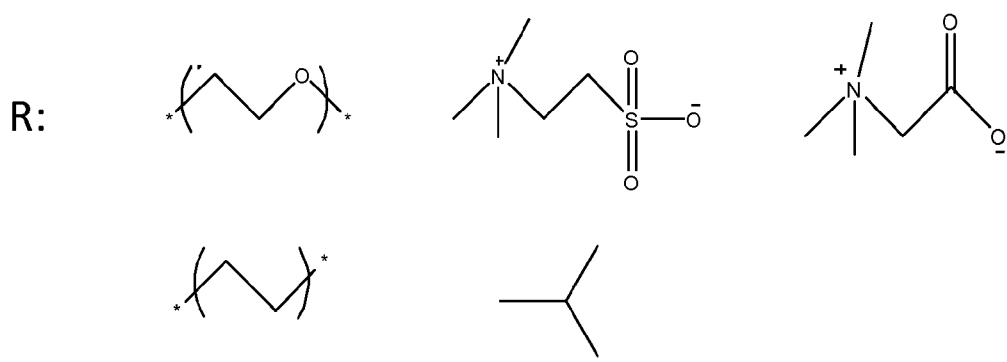
FIG. 2: Diagram showing monomer structures for use with Ring-opening metathesis polymerization.

A variety of monomers may be suited for use in methods of the invention. Exemplary monomers include, but are not limited to, lactic acid, epichlorohydrin, acrylate, methacylate, acrylamide, methacrylamide, norbornene, and oxanorbornene. Examples of monomer structures that may be used in ROMP, ATRP and RAFT according to the methods described herein are shown in FIGS. 1 and 2.

Figure 3:
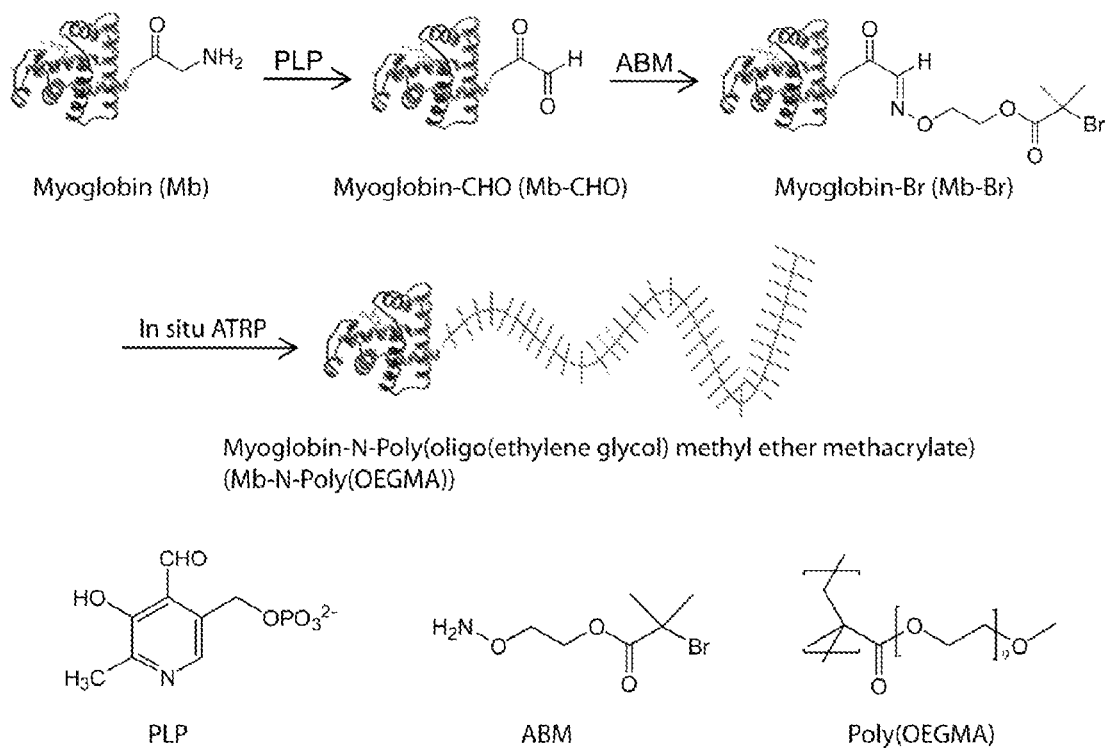
FIG. 3: Schematic illustration of in situ growth of stoichiometric poly(oligo(ethylene glycol) methyl ether methacrylate) (poly(OEGMA)) at the N-terminus of myoglobin. First, the N-terminus (glycine) is transformed to an aldehyde through a biomimetic transamination reaction (MB-CHO). Second, a hydroxylamine-functionalized ATRP initiator (ABM) is attached to the N-terminus, through a reaction between the aldehyde and the hydroxylamine, to form a macroinitiator (Mb-Br). Third, poly(OEGMA) is directly grown from the protein macroinitiator by atom transfer radical polymerization (ATRP).
Figure 4:
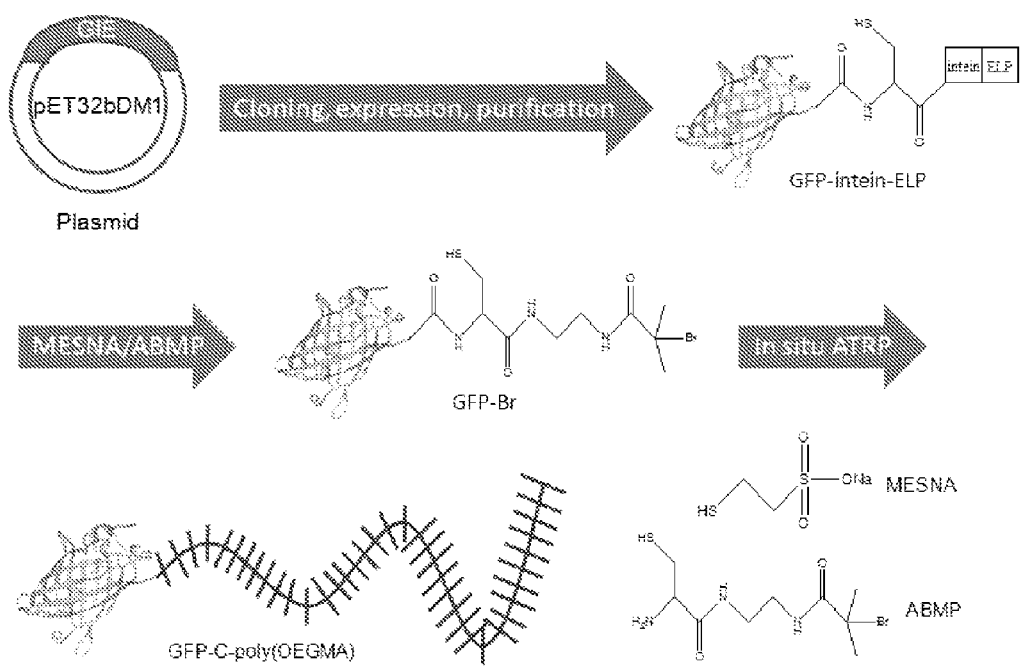
FIG. 4: Schematic illustration of preparing GFP-C-pOEGMA conjugates via in situ ATRP from the C-terminus of GFP.

For example, in situ growth of stoichiometric poly(oligo (ethylene glycol) methyl ether methacrylate) (poly (OEGMA)) at the N-terminus of myoglobin is schematically illustrated in FIG. 3. The N-terminus (glycine) is transformed to an aldehyde through a biomimetic transamination reaction (MB-CHO). A hydroxylamine-functionalized ATRP initiator (ABM) is attached to the N-terminus, through a reaction between the aldehyde and the hydroxylamine, to form a macroinitiator (Mb-Br) and poly(OEGMA) is directly grown from the protein macroinitiator by atom transfer radical polymerization (ATRP). A schematic illustration of GFP-C-pOEGMA conjugates prepared via in situ ATRP from the C-terminus of GFP, for example, is depicted in FIG. 4. In the scheme in FIG. 4, a genetically engineered GFP-intein-ELP is produced by cloning and expression in *E. coli* and purification by ITC. GFP is cleaved from intein-ELP with a mixture of MESNA and ABMP to form GFP-Br macroinitiator. poly(OEGMA) is grown in situ from the C-terminus of GFP by ATRP to form GFP-C-poly(OEGMA).

Figure 5:
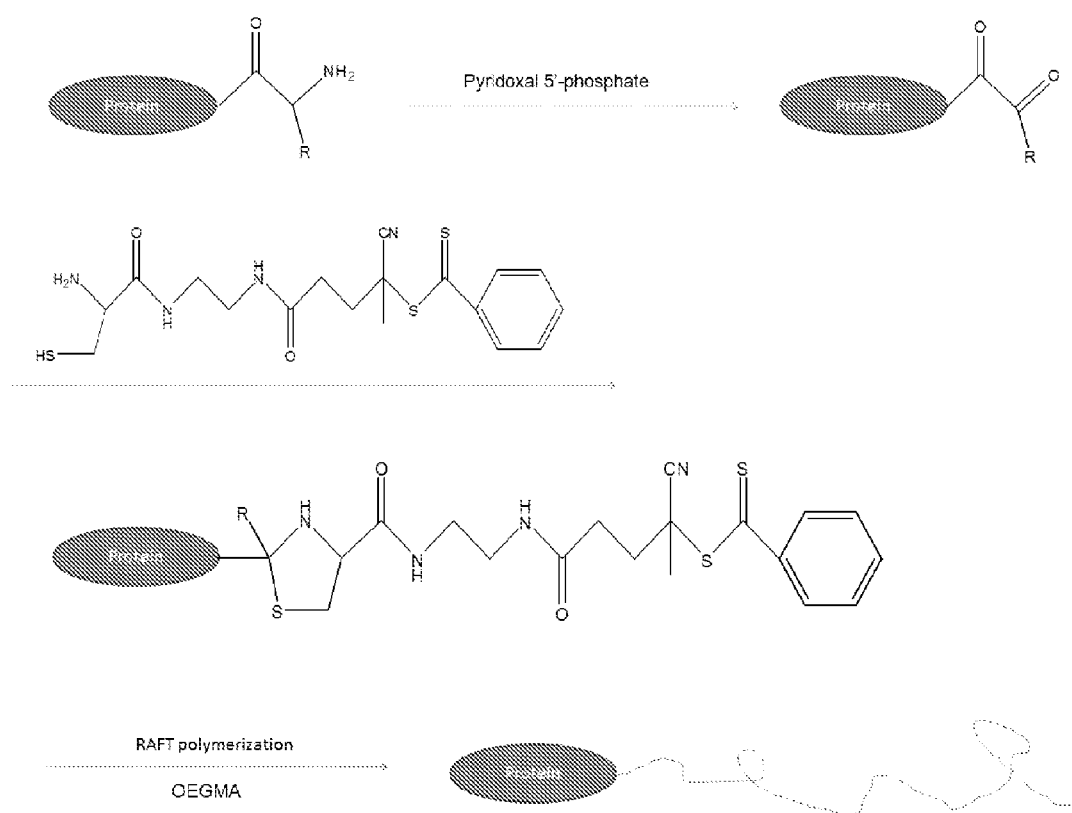
FIG. 5: Schematic illustration of preparing myoglobin-N-pOEGMA conjugates via in situ RAFT polymerization from the N-terminus of myoglobin.
Figure 6:
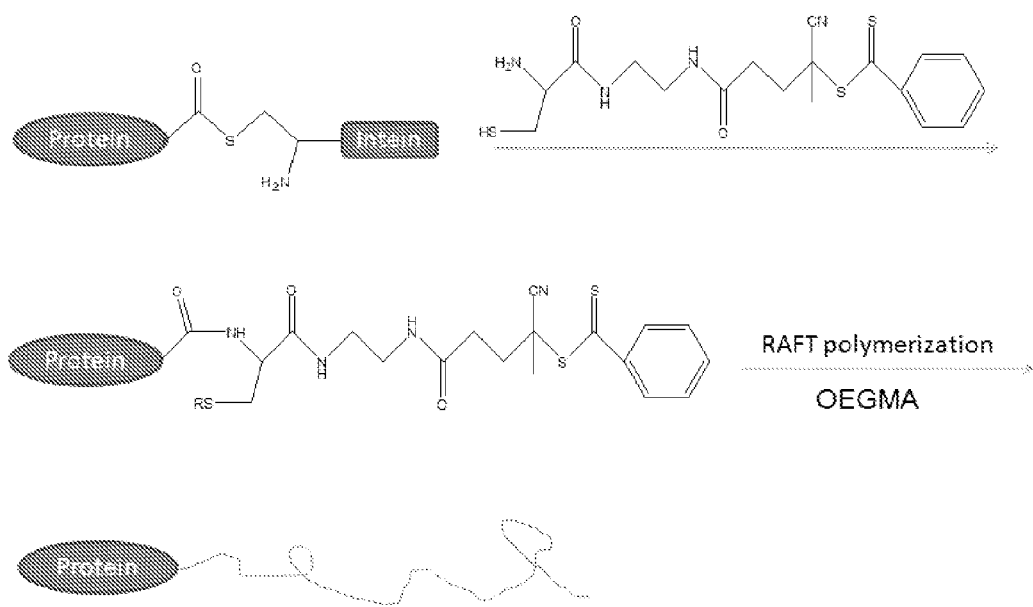
FIG. 6: Schematic illustration of preparing GFP-C-pOEGMA conjugates via in situ RAFT polymerization from the C-terminus of GFP.

A schematic illustration of myoglobin-N-pOEGMA conjugates prepared via in situ RAFT polymerization from the N-terminus of myoglobin, for example, is depicted in FIG. 5. A schematic illustration of GFP-C-pOEGMA conjugates prepared via in situ RAFT polymerization from the C-terminus of GFP, for example is depicted in FIG. 6.

The monomer may be, for example, non-biodegradable and/or hydrophobic. The monomer may include two reactive groups, both of which are reacted in order to form the polymer. For example, lactic acid includes two reactive groups, a hydroxy group and a carboxy group.

Monomers which contain one or more additional reactive groups may be incorporated into the polymer backbone. For example, a reactive monomer may be incorporated in the growing polymer chain by participating in the same types of chemical reactions as the growing polymer chain. For example, when lactide is being polymerized using a Lewis acid catalyst, a depsipeptide (cyclic dimer of an amino acid) can be prepared from lysine, in which the epsilon amine group is protected, for example, with a t-boc protecting group. The lysine is incorporated into the polymer, and the protecting group can be removed. The resulting amine groups are reactive with hydrophilic polymers which include leaving groups such as tosylates, tresylates, mesylates, triflates and other leaving groups well known to those of skill in the art.

Alternatively, the reactive monomer can include a leaving group that can be displaced with a nucleophilic group on a hydrophilic polymer. For example, epichlorohydrin can be used during the polymerization step. The monomer is incorporated into the polymer backbone, and the chloride group is present on the backbone for subsequent reaction with nucleophiles. An example of a hydrophilic polymer containing a nucleophilic group is a PEG with a terminal amine group. $PEG-NH_2$ can react with the chloride groups on the polymer backbone to provide a desired density of PEG-ylation on the polymer backbone. Using the chemistry described herein, along with the general knowledge of those of skill in the art, one can prepare polymer backbones which include suitable leaving groups or nucleophiles for subsequent coupling reactions with functionalized hydrophilic polymers.

Polymers may be polymerized in situ on the biomolecule or polypeptide at an initiation site using an initiator agent. An initiator agent is a molecule that assists in beginning the polymerization by interacting with the biomolecule and the monomer. Examples of initiator agents include those compatible with ATRP such as, without limitation, N-(2-aminoethyl)-2-bromo-2-methylpropanamide, N-(2-aminoethyl)-2-chloro-2-methylpropanamide, 2-bromo-N-(2-(2-hydrazinylacetamido) ethyl)-2-methylpropanamide, 2-chloro-N-(2-(2-hydrazinylacetamido) ethyl)-2-methylpropanamide. Examples of initiator agents also include those compatible with RAFT such as, without limitation, ZC(=S) SR, where R can be cysteine, hydrazine, hydroxylamine, and Z can be phenyl, alkyl, phthalimidomethyl. Examples of initiators also include those compatible with ROMP such as, without limitation, A-B, where A can be cysteine, hydrazine, hydroxylamine, and B can be olefins.

The methods may produce protein-polymer or polypeptide-polymer conjugates formed through site-specific modifications of the N-terminus or C-terminus of proteins or polypeptides with initiators such as ATRP initiators or RAFT agents, followed by in situ ATRP and RAFT polymerization from the initiators. The approach of modifying proteins with polymers using the N- or C-terminus facilitates attachment of the polymer in a controlled manner because each protein usually has an N-terminus and a C-terminus. For example, a unique initiator site comprising a thioester moiety may be generated by first incubating a polypeptide with intein such that intein binds at the C-terminus of the polypeptide, and cleaving the intein from the polypeptide. A unique initiator site may be generated by transferring the N-terminus of a polypeptide into an aldehyde through a biomimetic transamination reaction, followed by attachment of a functionalized initiator to the aldehyde N-terminus through a variety of coupling reactions.

In a protein or polypeptide, targets for polymerization may include side-chains of natural amino acid side-chains (such as lysine and cysteine) and non-canonical amino acid (such as N6-levulinyl lysine and para-azidophenylalanine) on the surfaces of proteins and specific interaction sites in proteins (such as streptavidin and avidin). Particular amino acids, such as the amine side-chain of lysine and the sulfhydryl group of cysteine may be targeted to synthesize protein-polymer conjugates via the "grafting from proteins" method. However, if a protein contains multiple lysines and cysteines on their surfaces this may lead to random modifications at multiple sites on the proteins, resulting in ill-defined biomolecule-polymer conjugates.

Polymerization may be facilitated by the inclusion of a catalyst solution. For example, ATRP catalyst system may include, but are not limited to, copper and ligands, where ligands can be derivatives of 2,2'-bipyridine, other π-accepting, chelating nitrogen-based ligands such as 2-iminopyridines and some aliphatic polyamines. RAFT catalyst system may include water soluble radical generating compounds, such as 4,4'-azobis(4-cyanopentanoic acid), 2,2'-Azobis[2-(2-imidazolin-2-yl)propane]dihydrochloride, 2,2'-Azobis[2-(2-imidazolin-2-yl)propane]-disulfate dehydrate, 2,2'-Azobis(2-ethylpropionamidine)-dihydrochloride. ROMP catalyst systems may include, but are not limited to, soluble Grubbs catalysts, such as tetraethylene glycol substituted ruthenium benzylidene, ruthenium alkylidene with triaryl phosphate ligands, or ruthenium alkylidene with ligands with quaternary ammonium. Other conditions used for polymerization may include, for example, that the polymerization be carried out under low oxygen, for example, under a noble or non-reactive gas such as argon, and/or for a time of at least about 5 min, at least about 15 min, at least about 60 min, and no more than about 12 hr, no more than about 24 hr, no more than about 48 hr. Polymerization may be carried out, for example, at a temperature of at least about 20° C., at least about 30° C., at least about 40° C., at least about 50° C., at least about 60° C., at least about 70° C., at least about 80° C., at least about 90° C. or at least about 100° C.

If desired, biodegradable regions may be introduced into the conjugates, constructed from monomers, oligomers or polymers using linkages susceptible to biodegradation, such as, for example, ester, peptide, anhydride, orthoester, and phosphoester bonds.

The biomolecule-polymer conjugates and polypeptide-polymer conjugates may be used in a number of different applications. For example, they may be used in prolonging the circulation of protein and peptide therapeutic agents in applications that include blood substitutes and targeting solid tumors. For example, they may be used as therapeutic agents, imaging agents, in proteomics, as protective coatings, in composite or smart materials, in sensors, and in the separation or purification of biomolecules, or for preconcentration or pre-processing of samples for assays of other diagnostic devices. Biomolecule-polymer conjugates made as described herein also may be useful in the treatment of diseases and conditions, including, for example, rheumatoid arthritis, Gaucher's disease, hyperuricemia, cancers, solid tumors, diabetes, Alzheimer's disease, hairy cell leukemia, multiple myeloma, venereal warts, AIDS-related Kaposi's sarcoma, chronic hepatitis B and C, inflammatory diseases, autoimmune diseases, infectious diseases and haemostatic disorders.

When used therapeutically, the biomolecule-polymer conjugates and polypeptide-polymer conjugates may have properties that result in improved targeted delivery of biomolecules to disease sites and may thus provide enhanced diagnostic and therapeutic efficacy of these compounds.

The biomolecule-polymer conjugates exhibit desirable properties over non-conjugated biomolecules, polypeptides and proteins, or over polymer conjugates formed using methods other than those described herein. For example, biomolecule-polymer conjugates produced as described herein may show improvement in one or more of solubility, stability, pharmacokinetics, immunogenicity and biodistribution or bioaccumulation at the cell, tissue, disease site, or organ level. The improved stability of the conjugates may manifest as an improvement in the half life compared with a comparable biomolecule that is not conjugated to a polymer.

The in vivo or serum half life may be improved. The improved half-life of the biomolecule-polymer may be at least about 25% greater, at least about 30% greater, at least about 40% greater, at least about 50% greater, at least about 60% greater, at least about 70% greater, at least about 80% greater, at least about 90% greater, at least about 100% greater, at least about 200% greater, at least 300% greater, at least 400% greater, or at least 500% greater than the in vivo half-life of the biomolecule when the biomolecule has not been conjugated to a polymer according to methods of the invention.

Improved stability may also manifest as an increased shelf life of the biomolecule, for example by reducing aggregation of the biomolecules. For example, after storage at 4° C. or 20° C. for a period of about one month, about three months or about a year, the biomolecule-polymer conjugate may show less than about 10%, less than about 20%, less than about 30%, less than about 40%, less than about 50%, less than about 60%, less than about 70%, less than about 80%, or less than about 90% of the aggregation that occurs when the biomolecule has not been conjugated to a polymer according to methods of the invention.

The improved solubility may manifest as an improvement in the solubility of the biomolecule-conjugate, such that the solubility of the biomolecule-polymer conjugate is at least about 25% greater, at least about 30% greater, at least about 40% greater, at least about 50% greater, at least about 60% greater, at least about 70% greater, at least about 80% greater, at least about 90% greater, or at least about 100% greater than the solubility of the biomolecule that has not been modified according to methods of the invention. Aggregation of biomolecules, such as proteins and polypeptides, may also be controlled or reduced by improving solubility of the biomolecule, polypeptide or protein according to methods of the invention The improvement in pharmacokinetics may include an improvement in one or more of the following: liberation of the biomolecule-polymer conjugate when administered in a formulation, absorption into the body, dispersion or dissemination of the biomolecule-polymer conjugate throughout the fluids and tissues of the body, and metabolism of parent compounds into daughter metabolites. For example, the conjugate may effect a reduction in metabolism of an active compound, or may stimulate metabolism of an inactive compound to form active metabolites and a reduced rate of excretion of an active compound from the body.

The improvement in immunogenicity may manifest as an improvement reduction in the immune response to a biomolecule, such that the biomolecule-polymer conjugate or polypeptide-polymer conjugate evokes at least about a 10% reduction, at least about a 20% reduction, at least about a 30% reduction, at least about a 40% reduction, at least about a 50% reduction, at least about a 60% reduction, at least about a 70% reduction, or at least about a 80% reduction in the immune response against the conjugate.

The in vivo biodistribution of the biomolecule-polymer conjugate, such as a polypeptide-polymer conjugate, to a cell, tissue, organ or disease site, such as a tumor or arterial plaque, may be increased compared with the biodistribution of the non-conjugated biomolecule. Biodistribution as used herein means the extent to which the conjugates accumulate in a cell, tissue, organ or disease site. For example, the biodistribution of the biomolecule-conjugate to a cell, tissue, organ or disease site may be at least about 10%, at least about 20%, at least about 25%, at least about 30%, at least about 40%, at least about 50%, at least about 60%, at least about 70%, at least about 80%, at least about 90%, at least about 100%, at least about 125%, at least about 150%, at least about 200%, at least about 300%, at least about 400%, or at least about 500% greater compared with the biomolecule not conjugated to a polymer.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Analytical Techniques Used in Examples 1 to 15

Materials

All chemicals and proteins were purchased from Sigma-Aldrich and used as received, unless otherwise specified. $^{125}$INa was purchased from Perkin-Elmer. Female nude mice (Balb/c nu/nu) were purchased from NCI (Frederick, Md.).

Size Exclusion Chromatography (SEC)

SEC was performed on a Shimadzu HPLC system equipped with a UV-vis detector (SPD-10A VP) and a refractive index detector (RID-10A), and a Asahipak GS-520 HQ (with a guard column) using Tris-HCl buffer (50 mM Tris, pH7.4) as the eluent at 20° C. (flow rate: 1.0 mL/min). Calibration was performed with PEG standards. Preparative SEC for isolation of conjugate was performed with an AKTA system (GE Healthcare) equipped with a Superdex 200 10/300 GL column using PBS as the eluent at a flow rate of 0.5 mL/min at 4° C.

Sodium dodecyl sulfate polyacrylamide gel electrophoresis (SDS-PAGE) SDS-PAGE were carried out using a Bio-Rad Ready Gel® Precast Gel System. Samples were prepared at 1 mg/ml concentration in TRIS buffer containing bromophenol blue and run though a precast Tris-HCl gradient gel (4-20%) under denaturing conditions (voltage 200 V, 500 mA, 50-55 min).

Electrospray-ionization Mass Spectrometry (ESI-MS)

ESI-MS measurements were carried out using a Thermo Finnigan LCQ Deca ion trap mass spectrometer (Thermo Finnigan, San Jose, Calif.). The instrument was calibrated with caffeine, MRFA, and Ultramark 1621 (all from Aldrich)

in the mass range 195-1822 Da. All spectra were acquired in positive ion mode over the mass to charge range, m/z, 100-2000 with a spray voltage of 5 kV, a capillary voltage of 44 V, and a capillary temperature of 275° C. Nitrogen was used as sheath gas while helium was used as auxiliary gas. The sample (1 mg/1 ml) was desalted and dissolved in water.

Matrix-assisted Laser Desorption Ionization Mass Spectroscopy (MALDI-MS)

An Applied Biosystems Voyager Systems 6154 mass spectrometer was used. Spectra were acquired in linear mode, and positive ions were generated using a $N_2$ laser. Protein samples were mixed with matrix (1:1 volume ratio, sinapinic acid, 10 µM) and air dried before analysis.

Liquid Chromatography/mass Spectrometry/mass Spectrometry (LC-MS/MS)

Approximately 2.5 µmol of myoglobin or green fluorescent protein (GFP) equivalent (by Bradford assay) of trypsin-digested Mb, Mb-CHO and Mb-Br was analyzed by LC-MS/MS using a Waters nanoAcquity and Thermo LTQ-Orbitrap XL mass spectrometer (Thermo Corporation). Peptides were separated on a 75 µm×250 mm BEH C18 column using a gradient of 5 to 40% v/v acetonitrile with 0.1% formic acid in 90 minutes, with a flow rate of 0.3 µL/min and column temperature of 45° C. Electrospray ionization was used to introduce the sample into the Orbitrap mass spectrometer in real time, with precursor ion scanning from 400 to 2000 m/z with 60,000 mass resolution. The top two precursor ions above a threshold of 10,000 counts were selected for MS/MS analysis in a data dependent fashion, and read out in the Orbitrap with 7500 resolution. Both precursor and product ion spectra are collected in a high-resolution, accurate-mass mode, allowing database searching to be performed at 10 ppm parent ion and 0.02 Da fragment ion mass tolerance.

UV-vis Spectroscopy

UV-vis spectra were recorded using a CARY 300 spectrophotometer (Varian) equipped with a temperature controller.

Fluorescence Spectroscopy

Fluorescence spectra were recorded using a CARY fluorescence spectrophotometer (Varian) equipped with a temperature controller.

Dynamic Light Scattering (DLS)

DLS of myoglobin and myoglobin-N-pOEGMA conjugates at 0.50 g/L in PBS, and GFP and GFP-C-poly (OEGMA) conjugates at 0.50 g/L in PBS were performed using a DynaPro LSR instrument (Protein Solutions, Charlottesville, Va.). The intensity versus intensity time correlation functions were measured at a scattering angle of 90° at 20° C.

Nuclear Magnetic Resonance (NMR) Spectroscopy $^1$H NMR measurements were performed using Varian INOVA-400 MHz multinuclear NMR at 25° C.

Inductively Coupled Plasma Optical Emission Spectrometry (ICP-OES)

Iron and copper contents in myoglobin and its polymer conjugate (10 µM in PBS) were analyzed by ICP-OES (Galbraith Laboratories, Inc.). The copper concentrations in native myoglobin (control) and the myoglobin-polymer conjugates were below the 0.02 ppm limit-of-detection of ICP-OES. The iron concentration in myoglobin (0.496 ppm) was found to be similar to that in the conjugate (0.546 ppm). These iron concentrations in both samples are quite close to those calculated from the protein concentrations. In addition, adding chelating agent EDTA did not remove iron from myoglobin.

Gamma Counter

Radioactivity was counted on a LKB1282 dual-channel gamma counter (Wallac, Turku, Finland).

Example 1

Synthesis of ATRP Initiators for Myoglobin Conjugates

N,N-Di(Boc)hydroxylamine. Anhydrous triethylamine (15 mL, 108 mmol, 1.1 eq.) was added at room temperature to a stirred suspension of O-benzylhydroxylamine.HCl (15 g, 94 mmol) in anhydrous acetonitrile (75 mL). After stirring for 1 h, the reaction mixture was filtered through a sintered glass filter funnel (medium porosity). The filter cake was washed with anhydrous acetonitrile (50 mL). The filtrate was then added drop-wise over 20 minutes to an ice-cooled solution of di-tert-butyl-dicarbonate (23.6 g, 108 mmol, 1.1 eq.) in anhydrous acetonitrile (75 mL). The reaction mixture was allowed to warm to room temperature and stir overnight (15 h). The following day, a solution of di-tert-butyl-dicarbonate (33.5 g, 153 mmol, 1.6 eq.) in anhydrous acetonitrile (75 mL) was added at room temperature. N,N-dimethylaminopyridine (1 g) was added and the reaction mixture was heated to 40° C. (oil bath temperature) for 5 h, and then dried under reduced pressure. The residue was suspended in ethyl acetate (150 mL), washed sequentially with 1M phosphate buffer (pH 7.4, 100 mL), saturated aqueous NaCl (100 mL), and then dried ($Na_2SO_4$). The drying agent was removed by filtration and the filtrate was concentrated under reduced pressure giving a white crystalline solid (30 g) that gave a single spot by thin layer chromatography ($R_f$=0.41, ethyl acetate:hexanes (1:5)) and was used without further purification. The solid (30 g) was dissolved in anhydrous methanol (375 mL). To this solution was added 5% Pd on $BaSO_4$ (3.2 g) and the resulting suspension was stirred under a balloon of hydrogen. After 20 h, thin layer chromatography (ethyl acetate:hexanes (1:5)) indicated complete consumption of the starting benzyl ether and the reaction mixture was filtered through a pad of Celite. The filter cake was washed with methanol (200 mL) and the filtrate was concentrated to dryness under reduced pressure giving N,N-Di(Boc)hydroxylamine ((Boc)$_2$NOH) as a white crystalline solid (21 g, 99%). $^1$H NMR (CDCl$_3$, 300 MHz): δ 1.49 (s, 18H). $^{13}$C NMR (CDCl$_3$, 300 MHz): δ 151.3, 84.7, 28.3. EIMS m/z: 256 ([M+Na]$^+$), 232 ([M–H]$^-$).

N-Boc-2-(aminooxy)ethanol. To a solution of (Boc)$_2$NOH (21 g, 90 mmol), in anhydrous N,N-dimethylformamide (30 mL) was added 2-bromoethanol (95%, 9.5 mL, 126 mmol, 1.4 eq.) and the resulting solution was cooled in an ice bath. Over a period of 15-20 minutes 1,8-diazabicyclo[5.4.0]undec-7-ene (20 mL, about 1.5 eq.) was added. The ice bath was removed and the reaction mixture was allowed to warm to room temperature and stirring was continued for 18 h. The reaction was diluted with H$_2$O (200 mL) and extracted with ethyl acetate (4×60 mL). The combined organic extracts were washed with saturated aqueous NH$_4$Cl (2×200 mL), saturated aqueous NaCl (2×100 mL) and dried (Na$_2$SO$_4$). The drying agent was removed by filtration and the filtrate was concentrated under reduced pressure giving a colorless oil (25 g), which was shown to be solely the product of N→O Boc transfer (33). This product was dissolved in methanol (150 mL) and cooled in an ice bath. Powdered KOH (85%, 9.2 g, 140 mmol) was added in one portion. The ice bath was removed and the reaction mixture was stirred for 1 h. The reaction was cooled once again in an ice bath and 12M HCl was added drop-wise until pH 7.0-7.5 (paper) was obtained. The reaction mixture was then filtered and concentrated under reduce pressure. The resulting oily residue was partitioned between H$_2$O (100 mL) and ethyl acetate (150 mL). The organic phase was washed with saturated aqueous NaCl (150 mL) and dried (Na$_2$SO$_4$). The drying agent was removed by filtration and the filtrate was concentrated under reduced pressure giving the desired product, N-Boc-2-(aminooxy) ethanol as a clear, pale oil (14.7 g, 92%). ($R_f$=0.40, ethyl acetate:hexanes (1:1)). $^1$H NMR (CDCl$_3$, 300 MHz): δ 7.42 (bs, 1H), 3.89 (t, J=4.5 Hz, 2H), 3.73 (t, J=4.5 Hz, 2H), 1.47 (s, 9H). $^{13}$C NMR (CDCl$_3$, 300 MHz): δ 158.8, 82.9, 78.4, 59.6, 28.3. EIMS m/z: 200 ([M+Na]$^+$), 216 ([M+K]$^+$).

NHS ester of 2-bromoisobutyric acid. A suspension of N-hydroxysuccinimide (20 g, 174 mmol) in anhydrous dichloromethane (300 mL) was cooled in a NaCl/ice bath. Diisopropylethylamine (30 mL, 174 mmol) was added in one portion followed by dropwise addition of 2-bromoisobutyryl bromide (22 mL, 174 mmol). The acid bromide was added at a rate such that the internal reaction temperature did not exceed 0° C. The ice bath was removed, the reaction mixture was stirred for an additional 45 minutes, and then concentrated to dryness under reduced pressure. The resulting solid residue was triturated and dissolved with diethyl ether (2×200 mL) and filtered. The filtrate was concentrated to dryness under reduced pressure, yielding the NHS ester as an amber solid (44 g, 96%). ($R_f$=0.74, ethyl acetate:dichloromethane (1:1)). $^1$H NMR (CDCl$_3$, 300 MHz): δ 2.82 (s, 4H), 2.03 (s, 6H). $^{13}$C NMR (CDCl$_3$, 300 MHz): δ 169.0, 167.7, 51.5, 30.9, 25.9.

N-Boc-(2-(aminooxy)ethyl) 2-bromo-2-methylpropanoate. A solution of N-Boc-2-(aminooxy)ethanol (14.5 g, 81.8 mmol) and the NHS ester of 2-bromoisobutyric acid (22.2 g, 84 mmol) in anhydrous dichloromethane (300 mL) was cooled in an ice bath. Anhydrous triethylamine (11.5 mL, 83 mmol, 1.01 eq.) and N,N-dimethylaminopyridine (1 g, 8.2 mmol, 10 mol %) were added. The ice bath was removed and the reaction was allowed to warm to room temperature and stirring was continued for 18 h. The reaction mixture was concentrated to dryness under reduced pressure giving a viscous oil, which was loaded onto a silica gel column (about 200 g SiO$_2$). Gradient elution (100% hexanes→15% ethyl acetate in hexanes) afforded the product as a pale, clear oil (20.8 g, 78%). ($R_f$=0.74, ethyl acetate:hexanes (1:2)). $^1$H NMR (CDCl$_3$, 300 MHz): δ 7.42 (s, 1H), 4.40 (apparent t, J=3.0 Hz, 2H), 4.05 (apparent t, J=3.0 Hz, 2H), 1.92 (s, 6H), 1.45 (s, 9H). $^{13}$C NMR (CDCl$_3$, 300 MHz): δ 172.2, 156.9, 82.1, 74.0, 63.3, 55.8, 31.0, 28.4. EIMS m/z: 348, ([M+Na]$^+$), 350 ([M+Na]$^+$).

(2-(aminooxy)ethyl) 2-bromo-2-methylpropanoate.HCl. A solution of the N-Boc protected hydroxylamine (14.8 g, 45.4 mmol) in anhydrous dichloromethane (70 mL) was cooled in an ice bath. To this solution was added 4 M HCl in 1,4-dioxane (120 mL, 480 mmol) at once via cannula. The ice bath was removed and stirring was continued for 1.5 h. The reaction mixture was concentrated to dryness under reduced pressure giving a thick pale yellow oil which crystallized upon standing at room temperature giving the final product as a white solid (11.8 g, 99%). $^1$H NMR (CD$_3$OD, 300 MHz): δ 5.0 (bs, 1H), 4.44 (m, 2H), 4.38 (m, 2H), 1.93 (s, 6H). $^{13}$C NMR (CD$_3$OD, 300 MHz): δ 172.6, 73.9, 63.7, 56.6, 31.0. EIMS m/z: 226 ([M−Cl]$^+$), 228 ([M−Cl]$^+$).

Example 2

Conjugation of ATRP Initiator to the N-terminus of Myoglobin (Mb)

Figure 7:
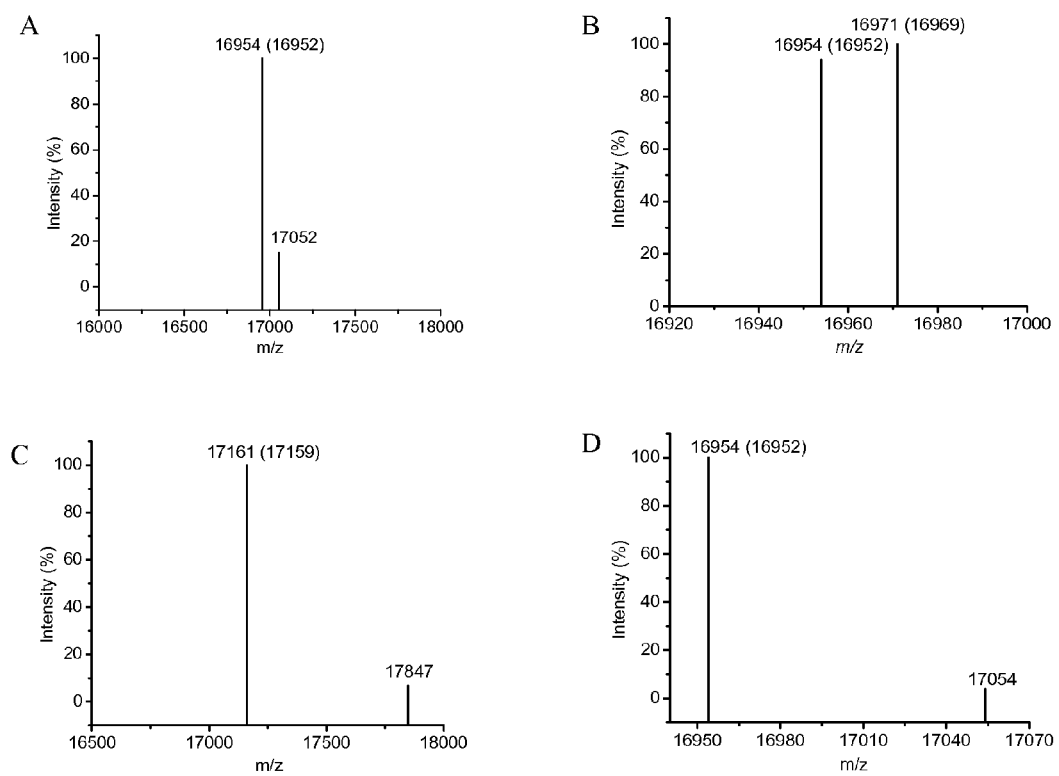
FIG. 7: Graphs showing ESI-MS data for Mb (A), Mb-CHO (B), Mb-Br (C), control (D). For the control sample, myoglobin (Mb) was directly reacted with ABM without prior reaction with PLP. Note that the value in parenthesis is the expected MW of the species.

A 50-mL Eppendorf tube was charged with a solution of Mb (25 mL of a 100 µM solution in 25 mM phosphate buffer, pH 6.5) and a solution of pyridoxal 5'-phosphate (PLP) (25 mL of a 20 mM solution in 25 mM phosphate buffer, pH adjusted to 6.5 with 2 M NaOH). The mixture was briefly agitated to ensure proper mixing, and was incubated without further agitation at 37° C. for 36 h. The PLP was removed from the reaction mixture via ultracentrifugation (Amicon Ultra-15 centrifugal filter; 3000 MWCO). The purified mixture (25 mL of a 50 µM solution in 50 mM phosphate buffer, pH 5.5) was treated with the ATRP initiator, (2-(aminooxy) ethyl) 2-bromo-2-methylpropanoate (ABM) (25 mL of a 2 mM solution in 50 mM phosphate buffer, pH 5.5) and allowed to sit without agitation for 36 h. The reaction solution was similarly purified by ultracentrifugation. In order to carry out ATRP from the N-terminus of Mb, a two-step procedure was used to attach the ATRP initiator solely to the N-terminal amine. (See FIG. 3) First, the protein was treated with pyridoxal-5-phosphate (PLP) in a phosphate buffer to yield an aldehyde at the N-terminus (Mb-CHO) through a transamination reaction. Two major peaks were observed by ESI-MS at 16954 and 16971 (FIG. 7B).

Figure 8:
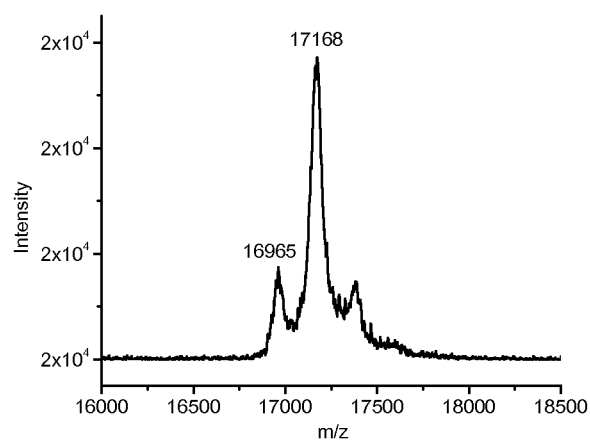
FIG. 8: Graph showing MALDI-MS analysis of Mb-Br. Two peaks at 16965 and 17168 are close to the theoretical MW 16952/16951 and 17159 of Mb/Mb-CHO and Mb-Br, respectively.

Aldehydes can be catalyzed by acids to form hydrates, and the extent to which hydrates of aldehydes form gives a measure of the relative stability of aldehydes. This dynamic reaction may have led to the two peaks observed by ESI-MS. The peak at 16971 is likely due to the hydrate form of Mb-CHO, Mb-C(H)(OH)(OH), as its experimentally observed molecular weight (MW) of 16971 is consistent with the theoretical MW of 16969 of this species. The second peak at 16954 is likely to arise from two species, Mb-CHO (theoretical MW=16951) and unmodified Mb, as the ESI-MS determined mass of control, native Mb (FIG. 7A) was 16954 (theoretical MW=16952). Next, the mixture was treated with (2-(aminooxy)ethyl) 2-bromo-2-methylpropanoate (ABM). ESI-MS of the reaction mixture resulted in a single peak with a mass of 17161, which is in close agreement with the theoretical MW of 17159 of the expected oxime product, myoglobin-Br (Mb-Br) (FIG. 7C). The overall yield of the N-terminal attachment of the ATRP initiator was about 75% (FIG. 8), as seen by the area ratio of the peaks corresponding to Mb/Mb-CHO and Mb-Br. As a negative control, myoglobin was directly reacted with ABM without prior reaction with PLP and analyzed by ESI-MS. The MW of the control was determined to be 16954 (FIG. 7D), which is identical to that of Mb (FIG. 7A). The data show that Mb reacts with PLP to form Mb-CHO prior to reacting with ABM.

Example 3

Trypsin Digestion of Modified Myoglobin

Protein samples were analyzed using a mini-Bradford assay to determine protein concentration (Bio-Rad, Inc.) followed by concentration normalization, and brief digestion with trypsin (Promega) by incubation of protein with trypsin at a 25:1 (w/w) ratio for 1 h at 37° C. in a solution of 50 mM ammonium bicarbonate. Samples were then acidified in 0.1% formic acid to stop proteolysis. Approximately 2.5 µmol of myoglobin equivalent (by Bradford assay) was analyzed by LC-MS/MS using a Waters nanoAcquity and Thermo LTQ-Orbitrap XL mass spectrometer (Thermo Corporation). Peptides were separated on a 75 µm×250 mm BEH C18 column using a gradient of 5 to 40% v/v acetonitrile with 0.1% formic acid in 90 minutes, with a flow rate of 0.3 µL/min and column temperature of 45° C.

Electrospray ionization was used to introduce the sample into the Orbitrap mass spectrometer in real time, with precursor ion scanning from 400 to 2000 m/z with 60,000 resolution. The top two precursor ions above a threshold of 10,000 counts were selected for MS/MS analysis in a data dependent fashion, and read out in the Orbitrap with 7500 resolution.

Both precursor and product ion spectra were collected in a high-resolution, accurate-mass mode, allowing database searching to be performed at 10 ppm parent ion and 0.02 Da fragment ion mass tolerance. Tandem mass spectra (MS/MS) were extracted, and their charge state was deconvoluted and deisotoped using Rosetta Elucidator software, (version 3.2, Rosetta Bioinformatics, Seattle, Wash.). All MS/MS spectra were analyzed using Mascot (Matrix Science, London, UK; version 2.2.0). Mascot was set up to search SwissProt (version 55.6, mammalian taxonomy, 390696 sequences) with trypsin as the proteolytic enzyme. Mascot was searched with a fragment ion mass tolerance of 0.02 Da and a parent ion tolerance of 10 ppm. Oxidation of methionine was specified in Mascot as a variable modification. All raw data was imported into Rosetta Elucidator and the four LC-MS/MS runs (one per sample) were aligned and features extracted using the PeakTeller algorithm.

Database searching (described above) was used to assign peptide identifications to the quantified features. All peptides reported were unambiguously identified using MS/MS database searching, with the exception of the brominated N-terminal peptide, whose identity was confirmed by accurate mass and isotope distribution modeling. Relative quantitation of each of the Mb peptides in the four different samples was performed by comparing the extracted ion intensities between the samples.

Figure 9:
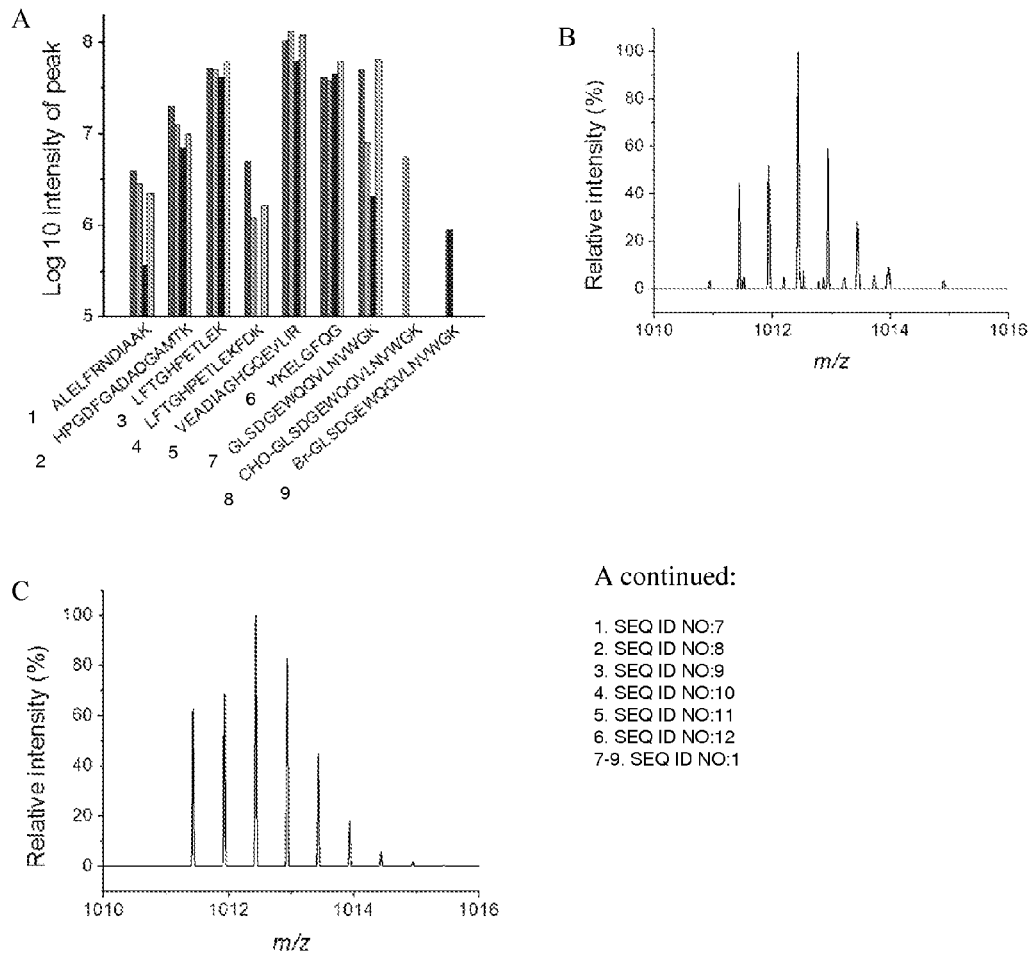
FIG. 9: Graphs showing analysis of peptide fragments by LC-MS/MS after trypsin digest. (A) Log10 intensity of myoglobin peptide fragments. Left column: Mb; Midleft column: Mb-CHO; Mid-right column: Mb-Br; Right column: control. Note: Log10 =5 is the approximate S/N limit. (B) Measured isotope distribution of [* BrGLSDGEWQQVLNVWGK]$^{2+}$ (SEQ ID NO:1), m/z =1011.4377, and mass measurement error is 3.46 ppm. (C) Theoretical isotope distribution of [*Br- GLSDGEWQQVLNVWGK]$^{2+}$(SEQ ID NO:1), m/z = 1011.4332.

The site-specificity of the modification at the N-terminus was confirmed by subjecting Mb, Mb-CHO and Mb-Br to a proteolytic digest with trypsin. Myoglobin was also directly reacted with ABM without prior reaction with PLP and then digested with trypsin as a negative control. A N-terminal fragment with an aldehyde was observed only for Mb-CHO (FIG. 9A) by analysis of the resulting peptide fragments by liquid chromatography/mass spectrometry/mass spectrometry (LC-MS/MS), which indicated that only the N-terminus of Mb was modified after reaction with PLP, leaving the 19 other amine groups in the lysine side-chains unaffected. Furthermore, a N-terminal peptide fragment with a bromine was only observed for Mb-Br (FIG. 9A), which confirmed the successful modification of the aldehyde with ABM. The experimental isotopic distribution of the fragment (FIG. 9B) was comparable to the theoretical Br isotopic distribution (FIG. 9C), which further confirmed the incorporation of Br into this N-terminal fragment. The peptide fragments from the control sample were experimentally indistinguishable from those observed for unmodified Mb, indicating a lack of reaction between ABM and Mb without prior treatment of Mb with PLP. These data confirm that the ATRP initiator was solely attached to the N-terminal amine of the protein to form a N-terminal brominated macroinitiator (Mb-Br) despite the presence of 19 lysine residues in the protein. After reaction, residual PLP and ABM were removed by centrifugal ultrafiltration with a cut-off molecular weight of 3,000 Da.

Example 4

In Situ ATRP from the N-terminus of Myoglobin

A deoxygenated solution of 1 mL PBS, 1.05 mmol poly (ethylene glycol) methyl ether methacrylate (OEGMA) (MW=475, Sigma-Aldrich), 0.02 mmol CuCl, 0.044 mmol $CuCl_2$, and 0.087 mmol 1,1,4,7,10,10-hexamethyltriethylenetetramine (HMTETA) was transferred into a deoxygenated myoglobin-Br (Mb-Br) solution in PBS. The polymerization was allowed to proceed for a given time under argon and then exposed to air. The polymerization mixture was further purified with HPLC (AKTA, GE Life Science) using a size exclusion column.

In situ ATRP of OEGMA was next carried out from Mb-Br in buffer. The progress of ATRP was monitored by size exclusion chromatography (SEC) as a function of polymerization time (FIGS. 10A-C), and by sodium dodecyl sulfate polyacrylamide gel electrophoresis (SDS-PAGE) analysis (FIG. 11). Refractive index (RI) and UV-visible absorbance detection at 280 nm (mainly protein) and 409 nm (HEME absorbance) allowed the protein (a mixture of unmodified Mb, and residual Mb-CHO and Mb-Br), to be discriminated from poly(OEGMA) and the Mb-N-poly(OEGMA) conjugate in the polymerization mixture. The SEC traces for both RI (FIG. 10A) and absorbance at 280 nm and 409 nm (FIGS. 10B and 10C) show the appearance of a new peak with a lower overall elution time than the peak corresponding to Mb; furthermore, this peak shifted to lower elution times with increasing polymerization times. The lower overall elution time of this peak is consistent with the in situ formation of a higher molecular weight (MW) Mb-N-poly(OEGMA) conjugate and the shift of this peak to lower elution time with increasing ATRP time suggests increasing MW of the polymer in the conjugate. The absorbance traces at 280 nm and 409 nm in FIGS. 10B and 10C ("d" traces) show that the polymerization mixture was composed primarily of the protein-polymer conjugate (about 70% by molar fraction) and a smaller (about 30%) fraction of residual protein (Mb, MB-CHO and Mb-Br). The 70% conversion efficiency of the protein to conjugate was close to that observed for the cumulative efficiency of conversion of the Mb to Mb-Br, and indicates that the initiation efficiency of the in situ ATRP from Mb-Br was nearly quantitative. SDS-PAGE analysis also showed that the bands for Mb-poly (OEGMA) conjugates had a larger MW than for Mb-Br (FIG. 11) and increased with increasing polymerization times, which confirmed both the polymerization of OEGMA from Mb-Br and the increase in the MW of the polymer with increasing polymerization time.

Figure 12:
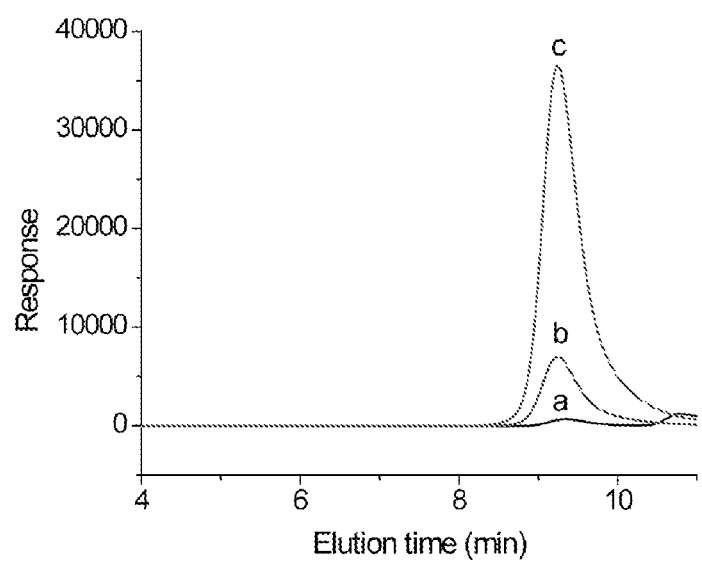
FIG. 12: Graph showing SEC traces of a control sample of native Mb used as a macroinitiator for ATRP for 1.5 h. a: Refractive index trace; b: UV absorbance trace at 280 nm; and c: UV absorbance trace at 409 nm.

In a control experiment, in which native Mb was used as an initiator for ATRP under the same polymerization conditions as were used for Mb-Br, the SEC peak traces of the protein did not shift to lower elution times even after 1.5 h (FIG. 12), indicating that ATRP did not occur without an ATRP initiation site on the protein. The third peak with the longest elution time of 10.5 min in FIG. 10A corresponds to phosphate, sodium chloride or other small molecules, which have a different refractive index from the mobile phase. The absence of a peak corresponding to free polymer indicated that removal for residual ABM from the polymerization mixture was successful and ATRP was carried out in a controlled manner, so that there was no free polymer generated in these ATRP experiments.

Figure 13:
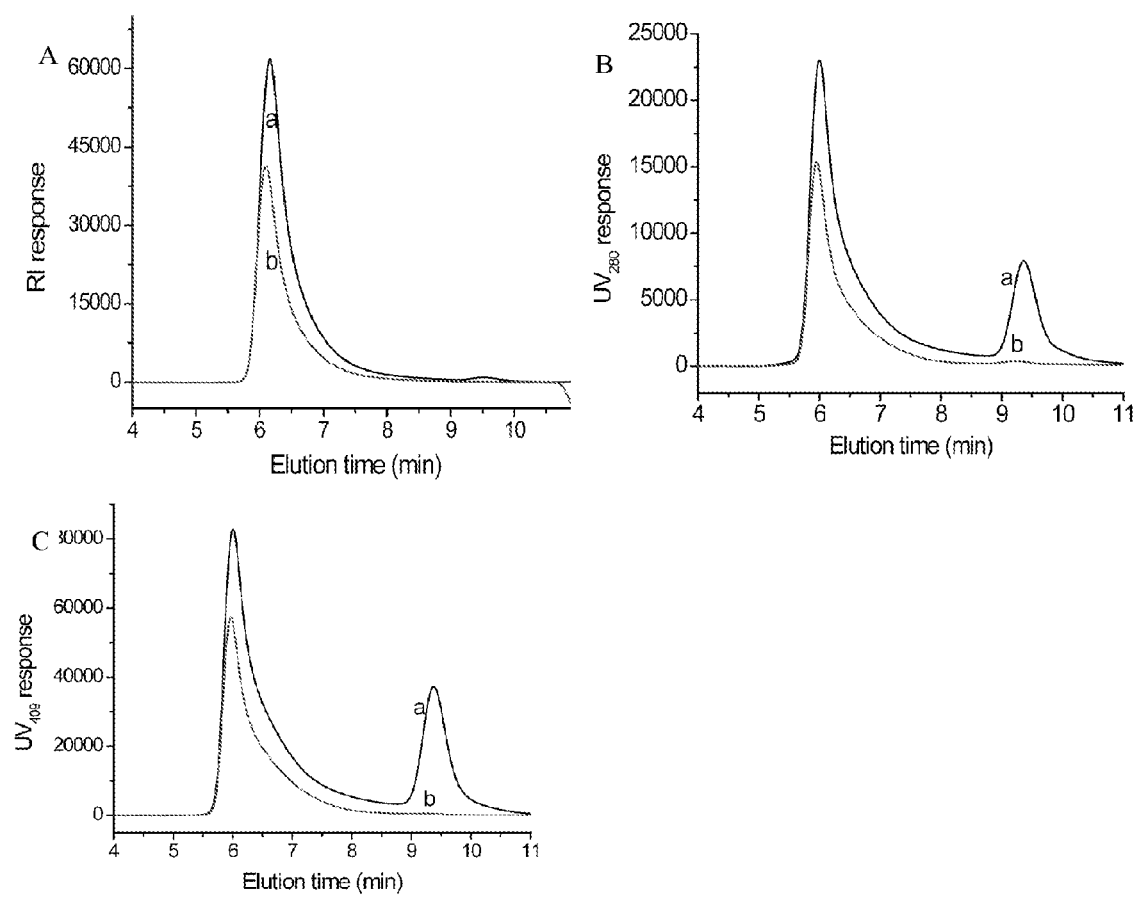
FIG. 13: Graph showing purification and characterization of Mb-N-poly(OEGMA). The polymerization mixtures were purified by SEC. (A-C) The SEC traces from RID, UVD at 280, 409 nm, wherein a and b correspond to samples of 60 min ATRP solution and purified Mb-N-poly(OEGMA), respectively.
Figure 14:
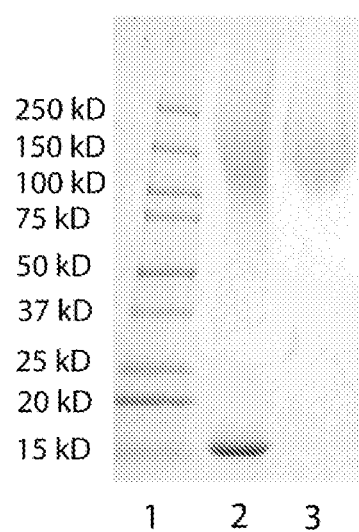
FIG. 14: Photograph showing SDS-PAGE analysis with Coomassie staining, before and after purification. Lane 1: Protein markers; Lane 2: Mb-N-poly(OEGMA), 60 min ATRP time; Lane 3: purified Mb-N-poly(OEGMA).

In order to further characterize the polydispersity and size of the conjugate, a Mb-N-poly(OEGMA) conjugate that was synthesized by in situ ATRP for 1.5 h was separated from the residual protein by size exclusion chromatography (SEC). The SEC trace for absorbance detection at 280 nm of the purified conjugate ("b" trace, FIG. 13B) showed only one peak corresponding to an elution time of 6 min and the absence of the peak corresponding to the unreacted Mb that was observed in the unpurified protein-polymer conjugate (FIG. 13: "a" trace, peak elution time about 9.3 min), showing that the unreacted protein had been completely removed from Mb-N-poly(OEGMA). These results were confirmed by absorbance detection at 409 nm (FIG. 13C) and RI detection as well (FIG. 13A). SDS-PAGE analysis provided visual confirmation of these results, as the band corresponding to Mb with a mass of about 17000 disappeared, and a smear of the Mb-poly(OEGMA) conjugate with a higher mass around 150 kDa was exclusively seen after purification by SEC (FIG. 14).

Figure 15:
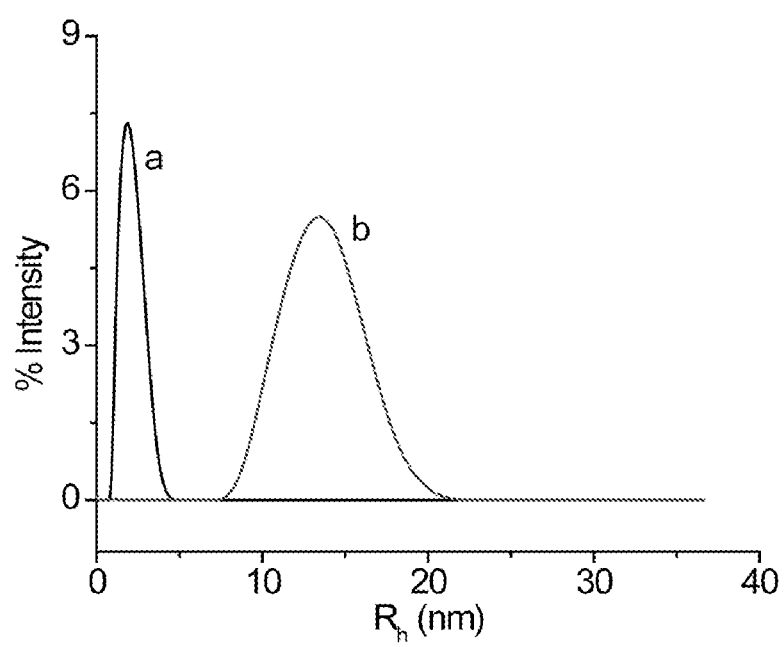
FIG. 15: Graphs showing DLS data of Mb (a) and Mb-N-poly(OEGMA) (b) in phosphate buffer solution.
Figure 16:
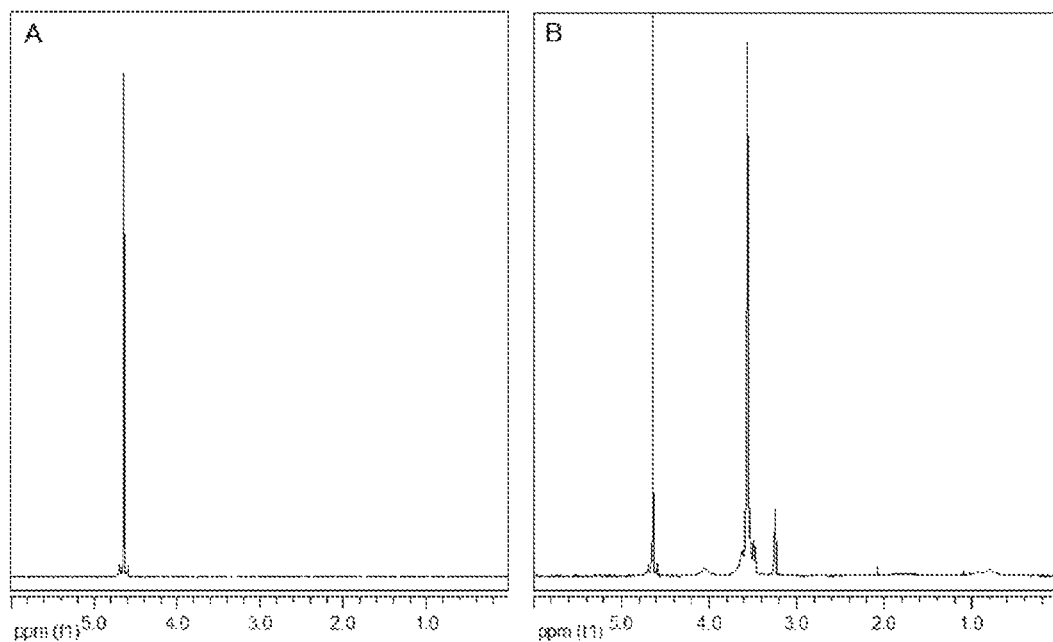
FIG. 16: Graphs showing $^1$H NMR spectra of Mb (A) and the purified conjugate (B).

The number-average molecular weight of the purified Mb-N-poly(OEGMA) conjugate with a polymerization time of 1.5 h was about 120 kDa, as determined by SEC calibrated with PEG standards, and the polydispersity of the conjugate was 1.4. The efficient purification of the conjugate from the protein was also confirmed by dynamic light scattering (DLS) which revealed only one distribution of particles with a hydrodynamic radius ($R_h$) of 13 nm with a polydispersity of 11.2% after purification, and the absence of a species corresponding to myoglobin, which has a Rh of 1.7 nm as shown in FIG. 15. $^1$H NMR analysis of the conjugate confirmed the synthesis of poly(OEGMA) from the protein (FIG. 16). Characteristic signals of poly(OEGMA) were observed at 1, 2, 3.4, 3.6-3.8, 4.2 ppm that correspond to $CCH_3$, $CH_2C$, $OCH_3$, $OCH_2CH_2$, $C(O)OCH_2$, respectively. Note that the protein signals are not visible in the NMR spectrum under the conditions used for NMR analysis. Elemental analysis of the Mb-N-poly(OEGMA) conjugate indicated the absence of copper in the conjugate.

Example 5

Evaluation of Peroxidase Activity of Myoglobin

Hydrogen peroxide (5 µL, 40 mM) was added to 1 mL of a 1 µM solution of Mb or modified Mb in 100 mM phosphate buffer at pH 7.0. After 5 min incubation at 20° C., excess catalase from bovine liver (2 mg/mL, 5 µL) was added, and the solution was further incubated for 2 min to completely decompose the excessive hydrogen peroxide. 2,2'-azino-di-(3-ethyl)benzthiazoline-6-sulfonic acid (ABTS) (10 mM, 5 µL) was added to the solution. The oxidation reaction was monitored on a Cary-300 UV-visible spectrophotometer at 409 nm. Protein concentrations were determined by the BCA protein assay (Pierce).

Figure 17:
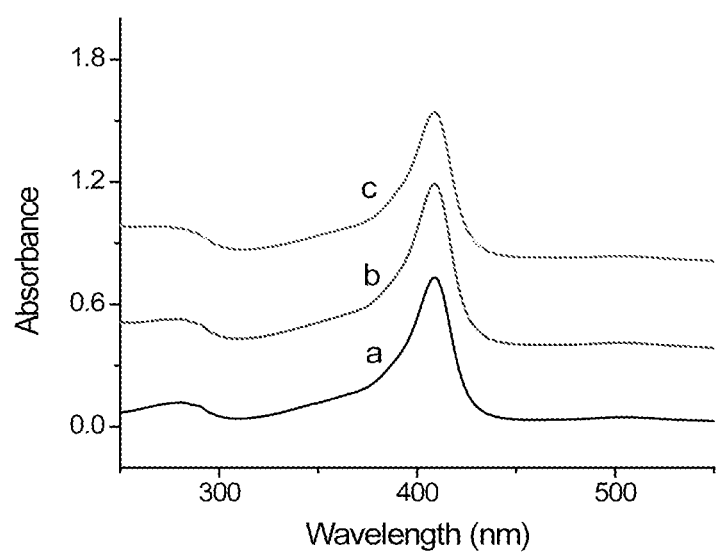
FIG. 17: Graph showing UV/Vis spectra of Mb (a), Mb-Br (b) and Mb-N-poly(OEGMA) (c) at the same concentration of 5 μM in phosphate buffer solution.
Figure 18:
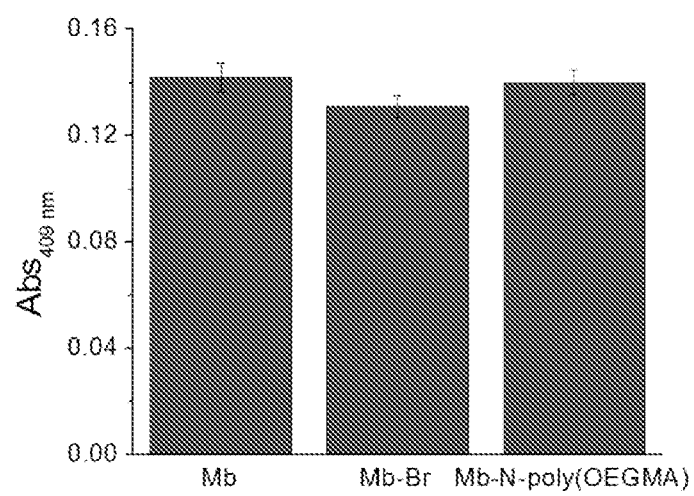
FIG. 18: Graph showing peroxidase activity of Mb, Mb-Br and Mb-N-poly(OEGMA).

The absorbance of the HEME prosthetic group at 409 nm of the conjugate relative to the native protein was measured. The absorbance of the HEME group at 409 nm was almost unchanged over the course of the reaction (FIG. 17), which indicated that the site-specific polymer conjugation of Mb at the N-terminus through in situ ATRP did not perturb the tertiary structure of the protein. The retention of the functional activity of the conjugate was further confirmed by quantifying the peroxidase-like activity of Mb. The absorbance at 409 nm was monitored by UV-visible spectrophotometry after treatment of Mb and modified derivatives with 2,2'-azino-bis(3-ethylbenzothiazoline-6-sulfonic acid) diammonium salt (ABTS) following reaction with hydrogen peroxide (FIG. 18). Mb, before and after the attachment of the ATRP initiator, showed almost the same activity, which was determined by comparing the absorbance at 409 nm of Mb at the same concentration of protein (1 µM). The original activity of Mb was also retained after the in situ synthesis of the poly(OEGMA) conjugate. These data indicated the peroxidase activity of Mb was retained after in situ growth of a stoichiometric (1:1) poly(OEGMA) conjugate at the N-terminal site.

Example 6

Attachment of Radiohalogens to Myoglobin

Iodination of myoglobin with $^{125}$I was performed with a Pierce IODO-Gen Pre-coated tube and purified by desalting on a dextran column (Pierce). 100 µL of 27 µM Mb (or conjugate) was added to 1 mCi $^{125}$INa loaded in IODO-Gen pre-coated tubes. The tubes were shaken every 30 s for 15 min. The iodinated protein or conjugate was purified by gel-filtration chromatography on a dextran column. The radioactivity was counted by a gamma-counter (LKB-Wallac, Turku, Finland) and the labeling efficiency was calculated by the equation:

% Efficiency=(Radioactivity of collected conjugate/ Total loaded radioactivity)×100.

Example 7

Pharmacokinetics of Myoglobin Conjugates

Seven nude mice bearing mouse breast carcinoma xenograft (4T1) were randomly divided into 2 groups. Group 1 (3 mice) and 2 (4 mice) received intravenous bolus injections of a given amount of PBS solution of $^{125}$I labeled Mb or Mb-N-poly(OEGMA) conjugate, respectively. Each animal was intravenously dosed with about 0.3 µg Mb (component) with about 5 µCi of $^{125}$I. Blood samples (20 µL) was collected from the tail vein of the mice at 40 s, 15, 30 and 60 min, 2, 4, 8, 24, 48 and 72 h after injection. The whole blood sample was analyzed by gamma-counting. The blood concentration time-course was analyzed with a standard two-compartment pharmacokinetic model to approximate both distribution and elimination of the samples. All animal experiments were performed in accordance with the Duke University Institutional Animal Care and Use Committee.

Figure 19:
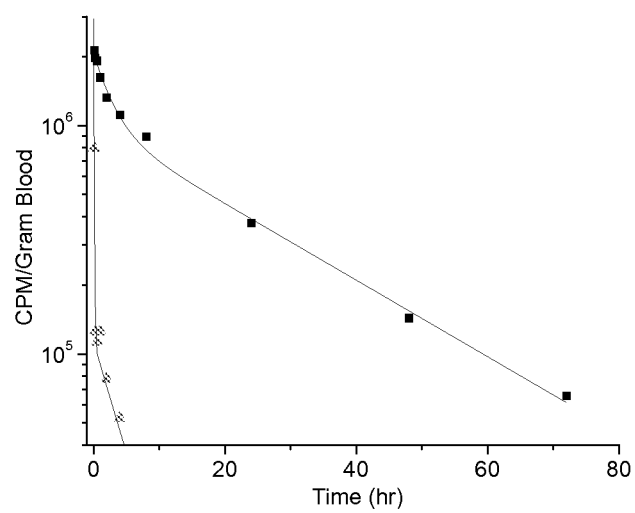
FIG. 19: Graph showing blood concentration as a function of time post-injection. After intravenous administration of $^{125}$I labeled Mb (triangle) and Mb-N-poly(OEGMA) (square), blood was sampled from the tail of mouse at given time points and quantified for radioactivity.

The pharmacokinetics of Mb and the purified Mb-N-poly (OEGMA) conjugate with a hydrodynamic radius of 13 nm were determined by intravenously administering $^{125}$I labeled Mb and conjugate to nude mice (Balb/c nu/nu), and collecting blood samples at various time intervals after administration (FIG. 19). A two-compartment model was used to fit the data. Distribution and elimination data were represented by the following parameters: area under the curve (AUC), total body clearance (CL) and blood half-life for the distribution and elimination phase ($t_{1/2\alpha}$, $t_{1/2\beta}$) (Table 1).

TABLE 1

Pharmacokinetic parameters calculated from a two-compartment model.

| Protein | $T_{1/2\alpha}$ (hr) | $T_{1/2\beta}$ (hr) | AUC (h*CPM/ml) | CL (ml/h) |
|---|---|---|---|---|
| Mb | 0.05 | 2.0 | $7.0 \times 10^5$ | 1.43 |
| Mb-N-poly(OEGMA) | 2.0 | 18 | $2.9 \times 10^7$ | 0.035 |

Figure 10:
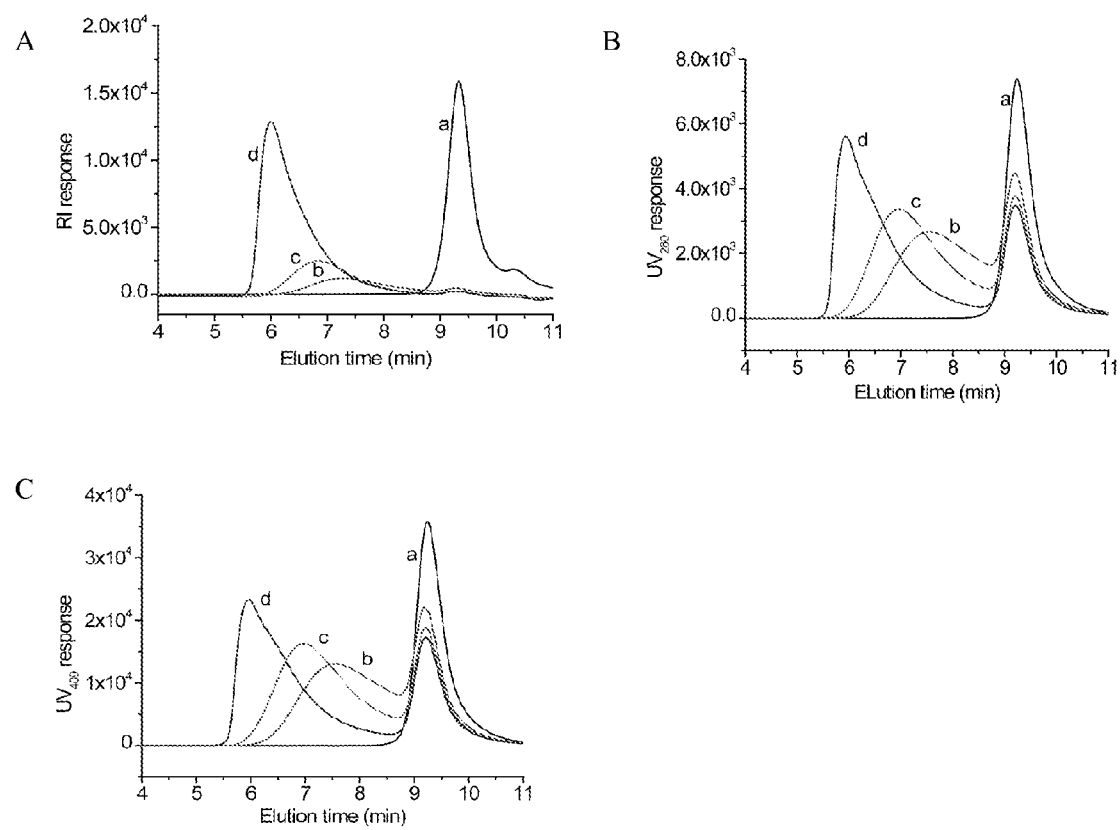
FIG. 10: Graphs showing in situ ATRP of OEGMA from the ATRP-initiator modified N-terminus of myoglobin as a function of polymerization time. The polymerization mixtures were directly analyzed by SEC with a refractive index detector (RID) and a UV detector (UVD). (A-C) The SEC traces detected by RID and UVD at wavelengths of 280 and 409 nm: Mb-Br (a), 5 min ATRP time (b), 15 min ATRP time (c) and 60 min ATRP time (d).
Figure 11:
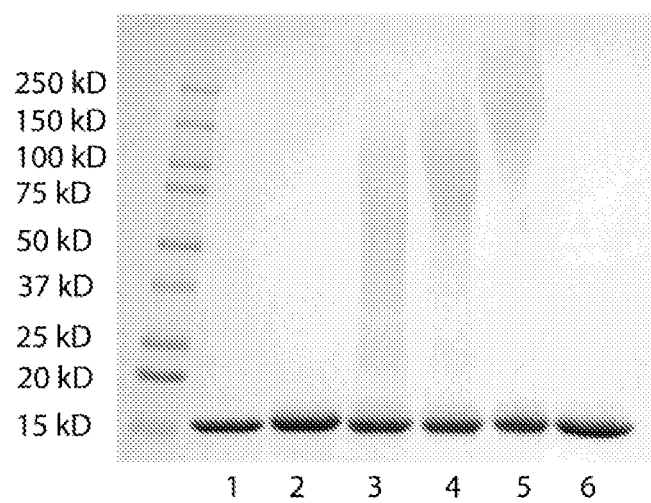
FIG. 11: Photograph showing SDS-PAGE analysis with Coomassie staining. Lane 1: Protein markers; Lane 2: Mb; Lane 3: Mb-Br; Lane 4: 5 min ATRP time; Lane 5: 15 min ATRP time; Lane 6: 60 min ATRP time; Lane 7: control: native Mb was used as an initiator for ATRP for 1.5 h. Images are shown for qualitative purposes.

The data in FIG. 10 were fit to a two-compartment model shown as a solid line, to quantify the elimination and distribution response of Mb and Mb-N-poly(OEGMA).

The pharmacokinetic parameters revealed a biphasic behavior (FIG. 10). After bolus administration, the concentration of unmodified Mb rapidly decreased in blood, with a short distribution phase ($t_{1/2\alpha}$=3.0 min) and a rapid terminal elimination phase ($t_{1/2\beta}$=2 h). In contrast, the distribution phase of poly(OEGMA) conjugation increased by 40 times ($t_{1/2\alpha}$=2 h), and the terminal elimination phase was prolonged to 18 h. There was also a difference in the clearance rate between Mb (1.43 mL/h) and Mb-N-polyOEGMA (0.035 mL/h). These differences in the pharmacokinetics resulted in a 41-fold greater area under the curve (AUC) for the Mb-N-poly(OEGMA) conjugate ($2.9 \times 10^7$ h*CPM/mL) as compared to myoglobin ($7.0 \times 10^5$ h*CPM/mL), indicating N-terminal site-specific conjugation with poly(OEGMA)

enhanced the cumulative exposure of Mb in the blood. The data show the polypeptide conjugates prolong the circulation of protein and peptide therapeutics in vivo.

Example 8

Synthesis of ATRP Initiator for GFP Conjugates

N-Boc-(2-aminoethyl)-2-bromo-2-methylpropanamide. A solution of N-Boc-ethylenediamine (5.0 mL, 32 mmol), and diisopropylethylamine (5.8 mL, 33 mmol) in anhydrous dichloromethane (35 mL) was cooled in a NaCl/ice bath (−10° C., bath temperature). Over a period of 15 minutes, 2-bromoisobutyryl bromide (4.1 mL, 33 mmol) was added to this solution. After 1 h, the ice bath was removed and the reaction was allowed to warm to room temperature and stirring was continued for 18 h. The reaction mixture was concentrated to dryness under reduced pressure giving a tan colored solid which was dry-loaded onto a silica gel column. The product was isolated by elution with ethyl acetate:dichloromethane (3:2) as an off-white solid (7.84 g, 80%). $^1$H NMR (CDCl$_3$, 300 MHz): δ 7.2 (bs, 1H), 4.91 (bs, 1H), 3.33 (m, 4H), 1.93 (s, 6H), 1.43 (s, 9H). $^{13}$C NMR (CDCl$_3$, 300 MHz): δ 172.9, 157.1, 80.1, 61.9, 42.0, 40.0, 32.5, 28.6. EIMS m/z: 331 ([M+Na]$^+$), 333 ([M+Na]$^+$).

N-(2-aminoethyl)-2-bromo-2-methylpropanamide.HCl. A solution of the N-Boc protected amide (7.84 g, 25.4 mmol) in 4 M HCl in 1,4-dioxane (64 mL, 256 mmol) was stirred at room temperature for 1 h. The reaction mixture was concentrated to dryness under reduced pressure giving an off-white white solid (6.2 g, 99%). $^1$H NMR (CD$_3$OD, 300 MHz): δ 8.36 (bs, 1H), 3.65 (bs, 1H), 3.51 (s, 2H), 3.09 (s, 2H), 1.94 (s, 6H). $^{13}$C NMR (CD$_3$OD, 300 MHz): δ 174.3, 58.9, 39.3, 37.8, 30.7. EIMS m/z: 209 ([M−Cl]$^+$), 211 ([M−Cl]$^+$).

2-Amino-N-[2-(2-bromo-2-methyl-propionylamino)-ethyl]-3-mercapto-propionamide (ABMP). N-(tert-butoxycarbonyl)-S-trityl-L-cysteine (10.2 g, 22.2 mmol) and N-(2-aminoethyl)-2-bromo-2-methylpropanamide.HCl (7.4 g, 30.4 mmol, 1.4 eq. mmol) were dissolved in a mixture of anhydrous dichloromethane (140 mL) and anhydrous N,N-dimethylformamide (80 mL). To this ice-cooled solution was added PyBOP (14.2 g, 27.4 mmol) and anhydrous triethylamine (dropwise, 6.4 mL, 44 mmol, 2 eq.). The reaction was allowed to warm to room temperature and stirring was continued for 22 h. The reaction mixture was concentrated to dryness under reduced pressure. Purification by silica gel flash column chromatography (2% methanol in dichloromethane) yielded the product as a glassy white solid (11.6 g, 80%). EIMS m/z: 673 ([M+Na]$^+$), 675 ([M+Na]$^+$). Deprotection was accomplished by stirring a mixture of the protected amide (9.3 g, 14.2 mmol), TFA (130 mL), H$_2$O (10 mL) and triisopropylsilane (10 mL) at room temperature for 15 minutes. The reaction mixture was concentrated to dryness under reduced pressure and the residue was partitioned between H$_2$O (100 mL) and dichloromethane (100 mL). The aqueous phase was washed with dichloromethane (2×100 mL) and concentrated to dryness (lyophilization) to give the desired product as a yellow glassy tar (5.8 g, 96%). $^{13}$C NMR of the free amine (CD$_3$OD, 300 MHz): δ 174.8, 168.7, 60.5, 56.2, 40.7, 40.3, 32.1, 26.3. EIMS m/z: 312 ([M−Cl]$^+$), 314 ([M−Cl]$^+$).

Example 9

Plasmid Construction and Protein Expression and Purification of Green Fluorescent Protein-intein-elastin-like Polypeptide (GFP-Intein-ELP)

The gene encoding for Mxe GyrA mini intein was amplified from template pTXB1(New England Biolabs) through PCR using Pfu polymerase (Fermentas) and 5'phosphorylated primers, Ph-CATGCGTATGTGCATCACG GGAGAT (SEQ ID NO:3) and Ph- GGCCTGAGTTCAGACCGGTGA (SEQ ID NO:4). The vector containing the GFP-ELP fusion structure (based on pET-32b, Novagen) was digested with Ball (Promega) to generate blunt-end fragments between the GFP and the ELP coding regions, and treated with calf intestinal phosphatase (Fermentas). The DNA fragments of the PCR product and the linearized vector were purified through agarose gel electrophoresis, and then linked together with T4 DNA ligase (Fermentas). The intein and ELP were linked by the same ten amino acids as in the pTXB1 vector (New England Biolabs), which separate the intein from the chitin binding domain in that system, followed by the amino acids that correspond to a His tag and a thrombin cleavage site, from the pET32a vector (Novagen). The ligation mixture was transformed into E. coli JM109, and recombinants containing the insert were the purity of the fusion proteins was approximately 95%, as ascertained by SDS-PAGE. identified by restriction endonuclease digestion and agarose gel electrophoresis to obtain the plasmid pTME (GFP-Intein-ELP). The sequence of the inserted Mxe intein was confirmed by automated nucleic acid sequencing. pTME was then transformed into E. coli expression BLR(DE3) competent cells (Novagen), and cultured in LB media supplemented with 100μg/ml of ampicillin. Induction of fusion protein expression was initiated when the OD600 reached 0.6, by adding IPTG to a final concentration of 0.3mM. The induction was carried out at a temperature of 20° C. overnight to minimize in vivo self-cleavage of the intein. Cells were harvested by centrifugation and sonicated (VirTis Corp.). Nucleic acids were removed from the crude extract using polyethyleneimine precipitation, followed by centrifugation. The inverse phase transition of the ELP fusion proteins was triggered by the addition of NaCI (0.25-3 M), and the aggregated ELP proteins were separated from the lysate by centrifugation at moderate temperatures (25-37° C.). The aggregated fusion proteins were resolubilized in cold PBS buffer, and the resolubilized protein solutions were centrifuged at 4° C. to remove any particulate contaminants. This aggregation and resolubilization process, called inverse transition cycle (ITC), was repeated 3-4 times until the purity of the fusion proteins was approximately 95%, as ascertained by SDS-PAGE.

Figure 20:
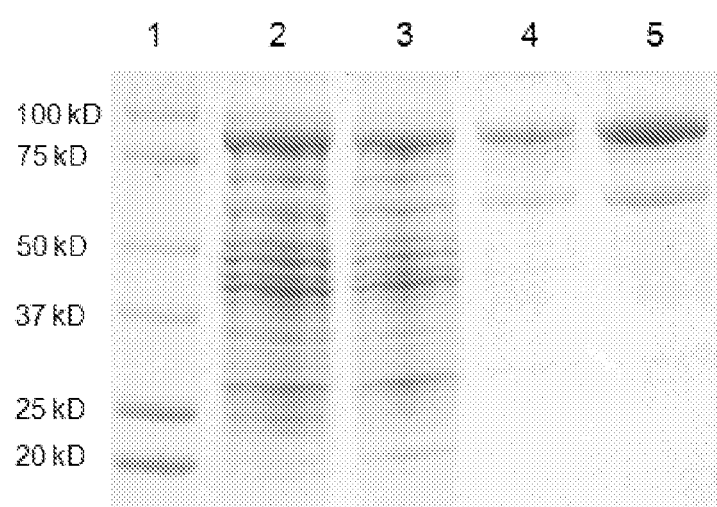
FIG. 20: Photograph showing SDS-PAGE analysis of GFP-intein-ELP expression and purification. In the left figure, Lane 1: protein marker; Lane 2: lysate; Lane 3: supernatant after adding PEI followed by cold spinning; Lane 4: re-dissolved pellet after 1 ITC; Lane 5: re-dissolved pellet after 2 ITCs.

FIG. 4 shows the schematic illustration of in situ growth of stoichiometricpoly(oligo(ethylene glycol) methyl ether methacrylate) (poly(OEGMA)) at the C-terminus of GFP. The plasmid of the fusion protein GFP-intein-ELP was constructed by recombinant DNA cloning techniques. After expression in E. coli. and purification by ITC, SDS-PAGE analysis (FIG. 20) shows two bands at 88,000 Da and 60,000 Da corresponding to GFP-intein-ELP and intein-ELP. This indicates that part of GFP-intein-ELP was natively cleaved in E. coli.

Example 10

Cleaving GFP from Intein-ELP with an ATRP Initiator ABMP 1 mL of a 250 μM GFP-Intein-ELP solution in 50 mM Tris-HCl buffer, pH 7.4 was mixed with 1 mL of 5 mM ABMP and 20 mM sodium-2-mercaptoethane sulfonate (MESNA) in Tris-HCl buffer and allowed to sit without agitation for 1 days at room temperature. The cleaved GFP-Br was purified by ITCs and ultrafiltration (Amicon ultra-15 centrifugal filter 3000 MWCO).

Figure 21:
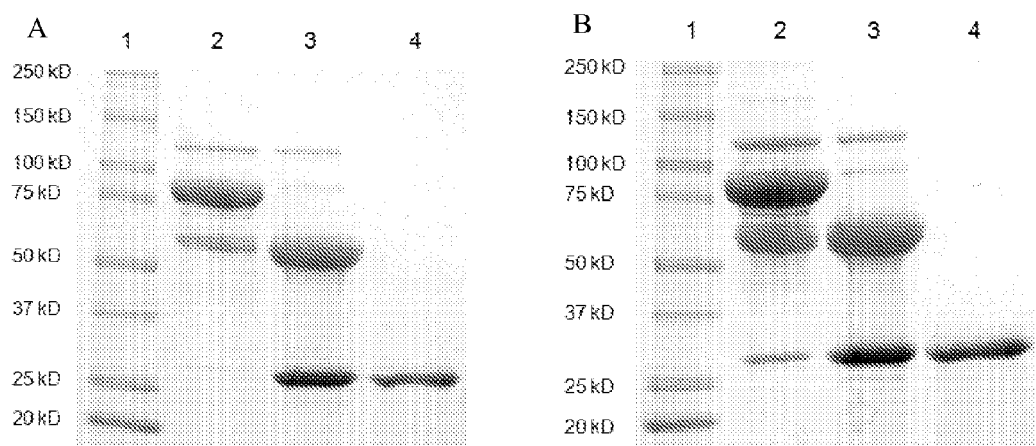
FIG. 21: Photograph showing SDS-PAGE analysis of cleavage of GFP from intein-ELP with a mixture of MESNA and ABMP (A), and MESNA (B). In the left figure, Lane 1: protein marker; Lane 2: GFP-intein-ELP; Lane 3: a mixture after intein cleavage; Lane 4: GFP-Br after purification by inverse transition cycling (ITC). In the right figure, Lane 1: protein marker; Lane 2: GFP-intein-ELP; Lane 3: a mixture after intein cleavage; Lane 4: GFP-SO$_3$H after purification by ITC.
Figure 22:
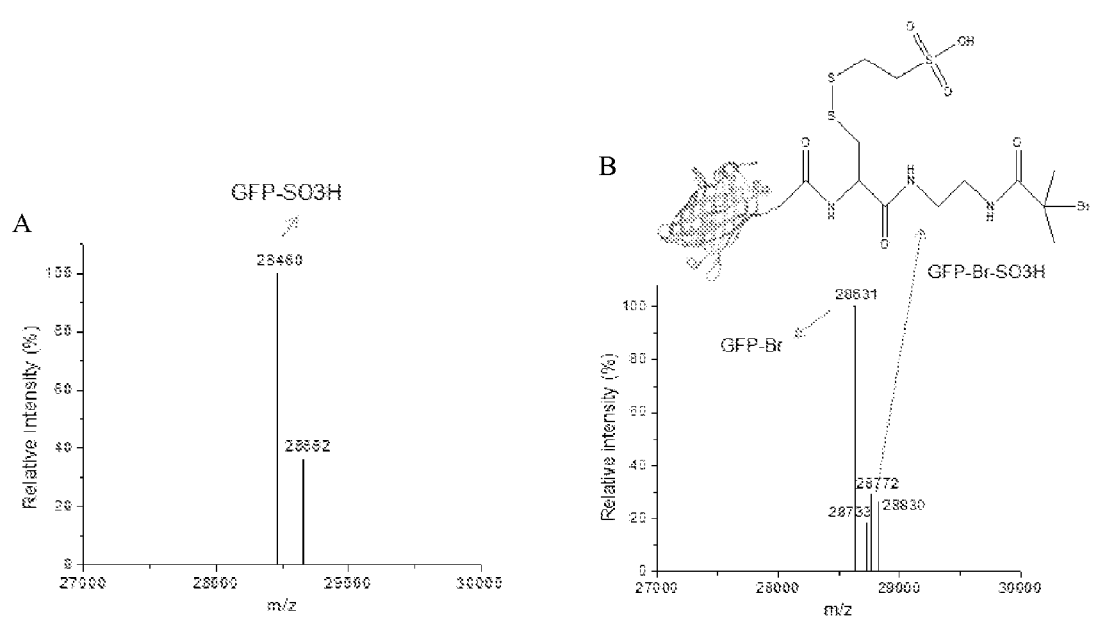
FIG. 22: Graph showing ESI-MS analysis of GFP-SO$_3$H (A) and GFP-Br (B). The measured MWs of GFP-SO$_3$H (28460) and GFP-Br (28631) are close to their theoretical mass of 28476 and 28650, respectively. In the right figure, the species GFP-Br—SO$_3$H with a mass of 28772 is likely to be a derivative of GFP-Br with a theoretical mass of 28788.
Figure 23:
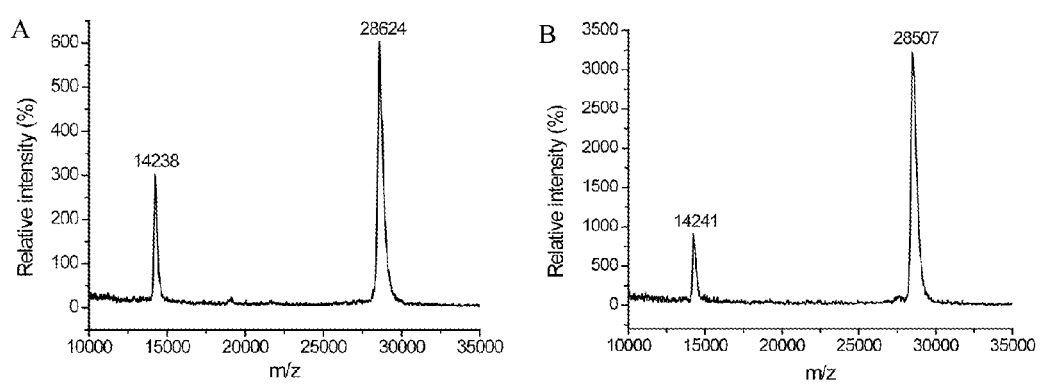
FIG. 23: Graph showing MALDI-MS analysis of GFP-Br (A) and GFP-SO$_3$H (B). The measured MWs of GFP-Br (28624) and GFP-SO$_3$H (28507) are close to their theoretical values 28650 and 28476, respectively.

GFP was cleaved off from intein-ELP with ABMP and MESNA to form GFP-Br (FIG. 21A). The cleaving efficiency was estimated to be 90%. As a control experiment, GFP was cleaved off with MESNA to form GFP-SO3H (FIG. 21B). ESI-MS and MALDI-MS analyses (FIGS. 22 and 23) show that the measured molecular weight of GFP-Br and GFP-SO$_3$H are closed to the theoretical values.

Example 11

Lys-C Digestion of GFP

Protein samples were analyzed using a mini-Bradford assay to determine protein concentration (Bio-Rad, Inc.) followed by concentration normalization, and brief digestion with Lys-C by incubation of protein with Lys-C at a 25:1 (w/w) ratio for 1 h at 37° C. in a solution of 50 mM ammonium bicarbonate. Samples were then acidified in 0.1% formic acid to stop proteolysis. Approximately 2.5 pmol of GFP equivalent (by Bradford assay) was analyzed by LC-MS/MS using a Waters nanoAcquity and Thermo LTQ-Orbitrap XL mass spectrometer (Thermo Corporation).

Figure 24:
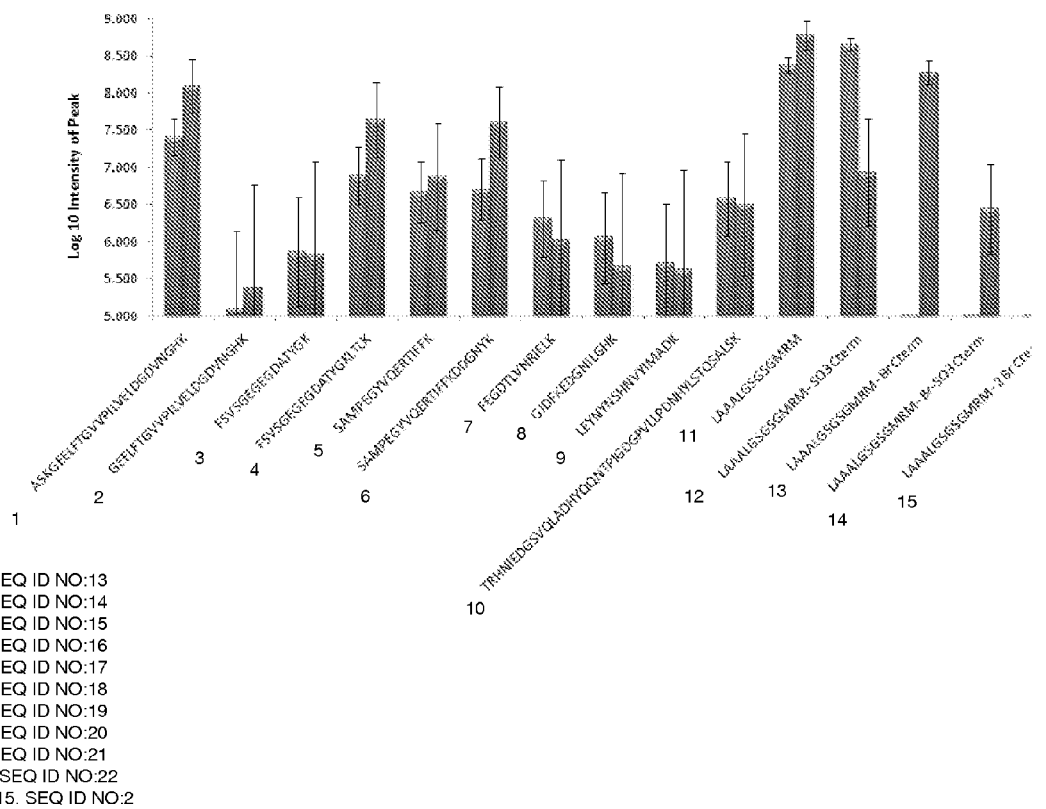
FIG. 24: Graph showing intensity (Log10) of GFP peptides as a function of sample. Left column: GFP-SO$_3$H; right column: GFP-Br. Analysis of the peptide fragments by LC-MS/MS showed that the reaction only occurred on the C-terminal fragment of the protein. GFP-SO$_3$H is a single product; however, GFP-Br has two derivatives GFP-Br—SO$_3$H and GFP-Br$_2$. In addition, GFP was observed in the two cases. Nevertheless, GFP and GFP-Br$_2$ has a very low content in the mixture so that they could not be observed in ESI-MS analysis. Note: Log10=5 is the S/N limit, so that below this threshold the data are not statistically significant.
Figure 25:
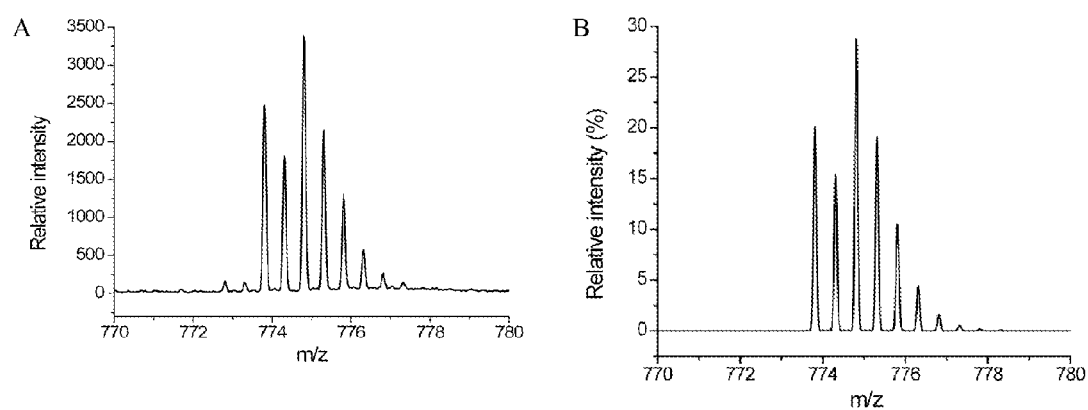
FIG. 25: Graph showing experimental isotope distribution: (A) of the C-terminal peptide K.LAAALGSGSGMRMMR M-Br,(SEQ ID NO:2) of GFP-Br, wherein M was oxidized. This is consistent with the theoretical isotope distribution (B), which further confirms the successful modification of the C-terminus of this modified peptide with the ATRP initiator.

As shown in FIG. 24, analysis of peptide fragments after Lys-C digestion indicates that the ATRP initiator was only attached at the C-terminal site although there are a small part of byproducts like GFP-Br—SO3H, GFP-SO3H and GFP-Br—Br. Furthermore, the isotope pattern of the bromine fragment is much close to the theoretical one (FIG. 25), meaning the bromine ATRP initiator was solely located at the C-terminus.

Example 12

In Situ ATRP from GFP-Br

A deoxygenated solution of 1 mL PBS, 1.05 mmol poly (ethylene glycol) methyl ether methacrylate (OEGMA) (MW=475, Sigma-Aldrich), 0.02 mmol CuCl, 0.044 mmol CuCl$_2$, and 0.087 mmol 1,1,4,7,10,10-hexamethyltriethylenetetramine (HMTETA) was transferred into a deoxygenated GFP-Br solution in PBS. The polymerization was allowed to proceed for a given time under argon and then exposed to air. The polymerization mixture was further purified with HPLC (AKTA, GE Life Science) using a size exclusion column.

Figure 26:
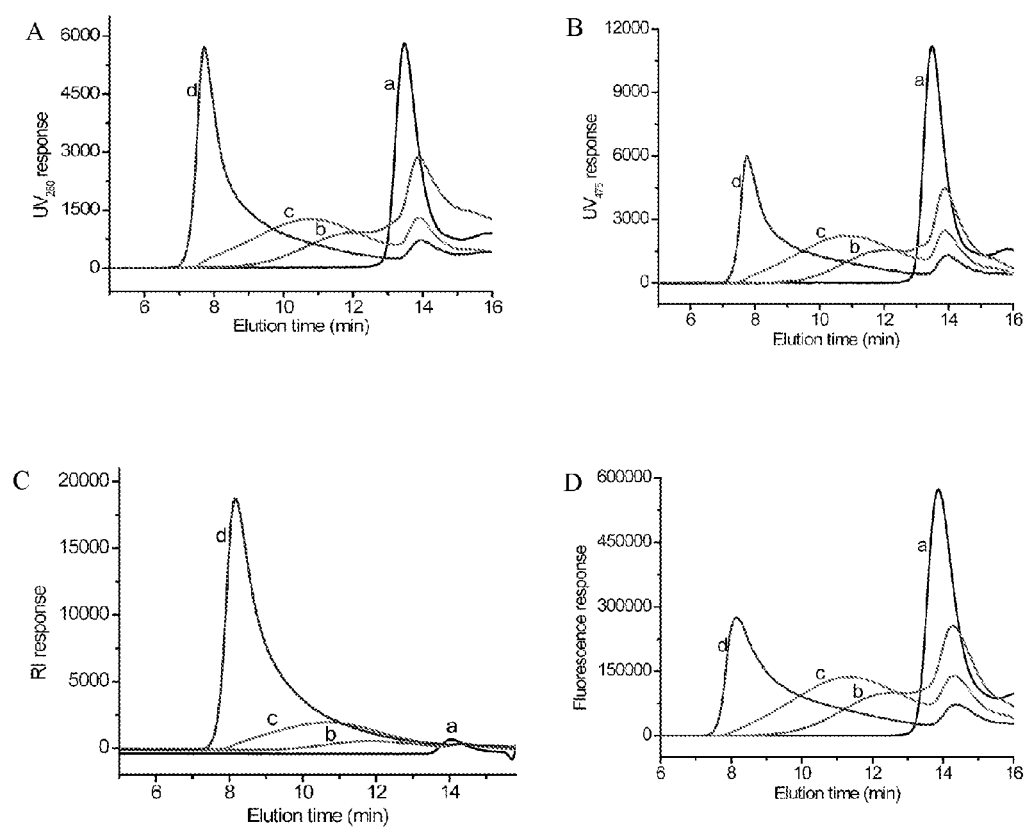
FIG. 26: Graph showing in situ ATRP of OEGMA from the ATRP-initiator modified C-terminus of GFP as a function of polymerization time. The polymerization mixtures were directly analyzed by SEC. a) GFP-Br; b) 5 min ATRP; c) 15 min ATRP; d) 120 min ATRP. A) SEC traces by UV detector at absorbance of 280 nm; B) SEC traces by UV detector at absorbance of 475 nm; C) SEC traces by reflective index detector; D) SEC traces by fluorescence detector with excitation at 460 nm and emission at 507 nm.
Figure 27:
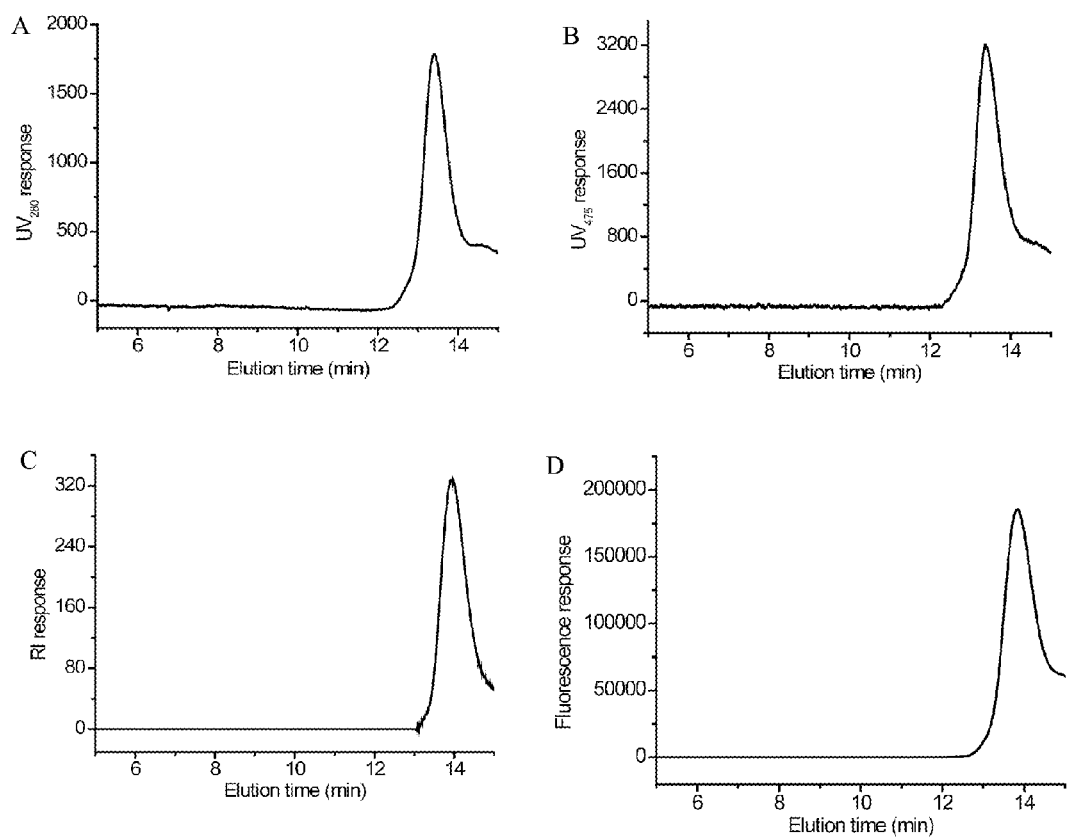
FIG. 27: SEC traces of a control sample where GFP-SO$_3$H was used as a macroinitiator for ATRP for 2 h. A) SEC trace by UV detection of the absorbance at 280 nm; B)SEC trace by UV detection of the absorbance at 475 nm; C) SEC trace by refractive index detection; D) SEC trace by fluorescence detection with excitation at 460 nm and emission at 507 nm.
Figure 28:
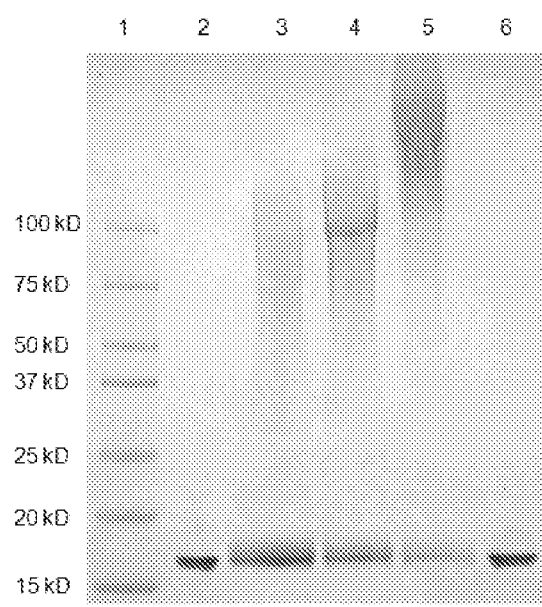
FIG. 28: Photograph showing SDS-PAGE analysis of GFP-Br, GFP-C-PolyOEGMA conjugates and control. Lane 1: Protein markers; Lane 2: GFP-Br; Lane 3: GFP-C-Poly-OEGMA, ATRP for 5 min; Lane 4: GFP-C-PolyOEGMA, ATRP for 15 min; Lane 5: GFP-C-PolyOEGMA, ATRP for 120 min; Lane 6: Control.
Figure 29:
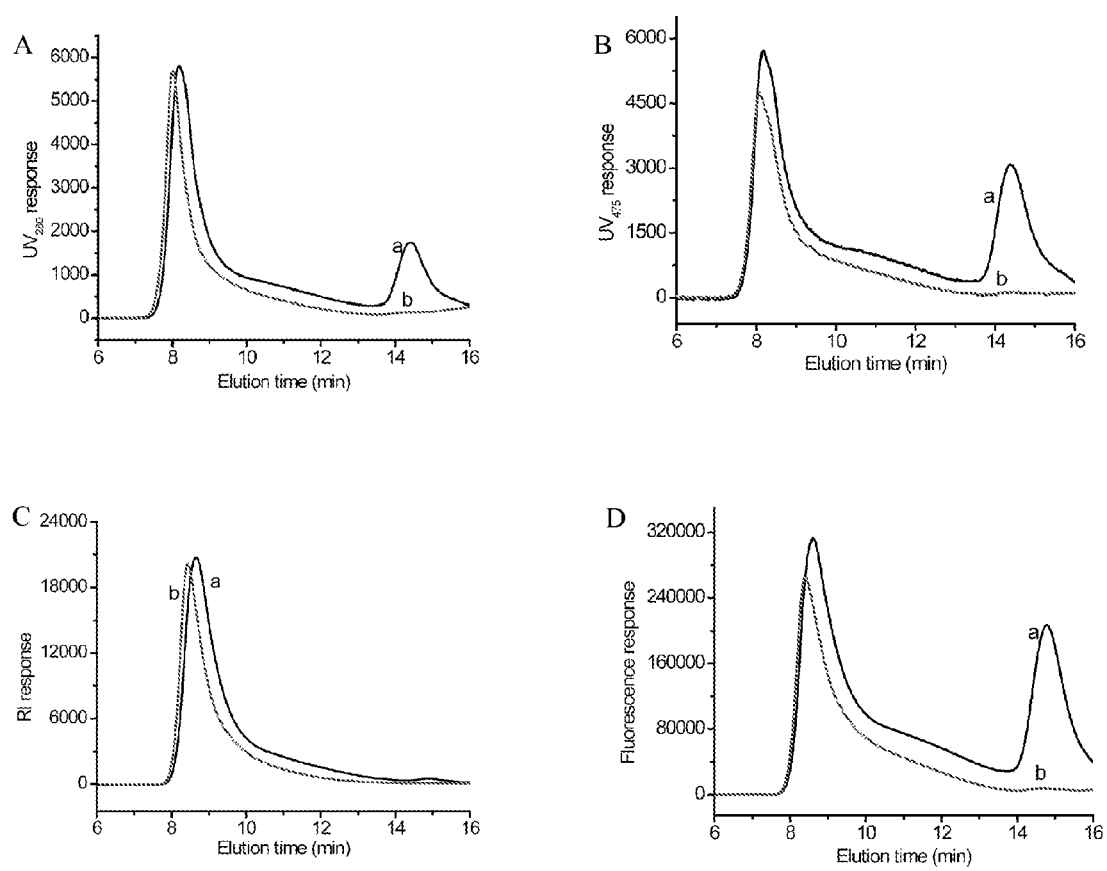
FIG. 29: Graphs showing SEC traces of GFP-C-poly (OEGMA) before and after purification. Traces a and b correspond to an unpurified sample that was polymerized for 120 min by ATRP and purified GFP-C-poly(OEGMA), respectively. A) SEC traces by UV detection of absorbance at 280 nm; B) SEC traces by UV detection of absorbance at 475 nm; C) SEC traces by refractive index detection; D) SEC traces by fluorescence detection with excitation at 460 nm and emission at 507 nm.
Figure 30:
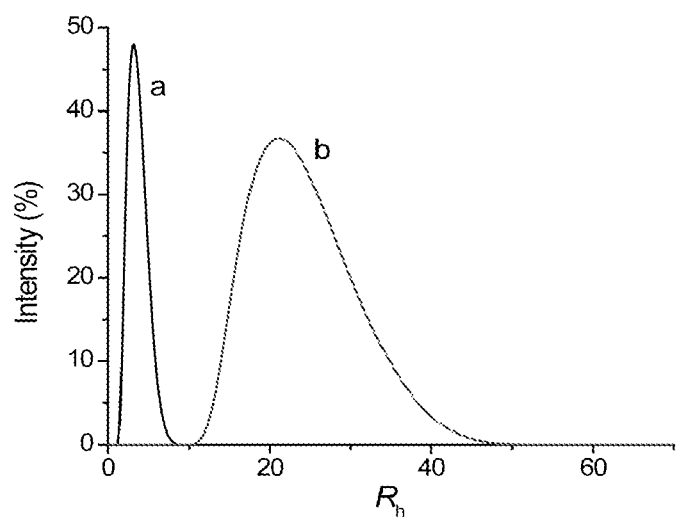
FIG. 30: Graph showing DLS data of: (a) GFP-Br, and (b) GFP-C-poly(OEGMA).
Figure 32:
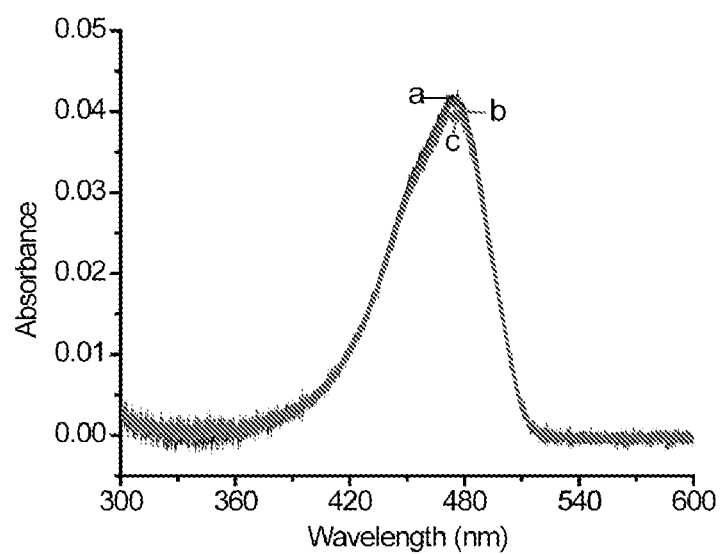

As shown in FIG. 26, after in situ ATRP, a new peak appeared at a short elution time and shifted to a lower value with increasing ATRP time, indicating poly(OEGMA) was in situ formed from the GFP-Br in a controlled manner. In the control experiment with GFP-SO3H as a initiator, no new peak was observed after 2 h (FIG. 27), indicating it is impossible to grow poly(OEGMA) from GFP without the ATRP initiator. SDS-PAGE data (FIG. 28) further confirm the growth of poly(OEGMA) solely from GFP-Br, not GFP. After purification with the AKTA purifier, the unreacted GFP components were completely removed from the conjugates (FIG. 29). The yield was estimated to be more than 80%. DLS measurements show that the hydrodynamic radius of GFP-Br was increased from 3.1 nm to 22 nm after 2 h ATRP (FIG. 30). $^1$H NMR spectra show the characteristic signals of poly (OEGMA) after in situ ATRP from GFP-Br, indicating the formation of poly(OEGMA) from the GFP-Br (FIG. 31). The UV absorbance and fluorescence spectra of GFP-C-poly (OEGMA) are very close to those of GFP-Br, meaning the 3-dimensional structure and activity of GFP were retained almost completely after in situ ATRP (FIGS. 32, 33).

Example 13

Attachment of Radiohalogens to GFP

Iodination of GFP with $^{125}$I was performed with a Pierce IODO-Gen Pre-coated tube and purified by desalting on a dextran column (Pierce). Briefly, 100 µL of 27 µM GFP (or conjugate) was added to 1 mCi $^{125}$INa loaded in IODO-Gen pre-coated tubes. The tubes were shaken every 30 s for 15 min. The iodinated protein or conjugate was purified by gel-filtration chromatography on a dextran column. The radioactivity was counted by a gamma-counter (LKB-Wallac, Turku, Finland) and the labeling efficiency was calculated by the equation:

% Efficiency=(Radioactivity of collected conjugate/ Total loaded radioactivity)×100

Example 14

Pharmacokinetics of GFP Conjugate

In a typical experiment 12 Balb/c mice were randomly divided into three groups with each group having 4 mice. Each animal was weighed before injection. The groups were received intravenous bolus injections of a given amount of PBS solution of $^{125}$I labeled GFP and GFP-C-poly(OEGMA) conjugates, respectively. Each animal was given intravenously the dose of 0.3 µg GFP (component) with a trace of $^{125}$I (~5 µCi). The injection volume of the sample solution was calculated by (Body weight/9)*51. Blood samples (10 µL) were collected from the tail vein of the mice at 40 s, 5 min, 15 min, 2 h, 4 h, 8 h, 24 h, 48 h and 72 h points after injection. The whole blood samples were analyzed by gamma counting. The blood concentration time-course will be analyzed with a standard two-compartment pharmacokinetic modal to approximate both distribution and elimination of the samples.

As shown in FIG. 34 and Table 2, after conjugation, pharmacokinetic parameters were greatly enhanced, which may have use in cancer and diabetes therapies. The data in FIG. 34 were fit to a two-compartment model shown as a solid line, to quantify the elimination and distribution response of GFP and GFP-C-poly(OEGMA).

TABLE 2

Pharmacokinetic parameters calculated from a two-compartment model.

| Protein | $T_{1/2\alpha}$ (hr) | $T_{1/2\beta}$ (hr) | AUC (h · CPM/ml) | CL (ml/h) |
|---|---|---|---|---|
| GFP (D = 5.2 nm) | 0.09 | 4.5 | $7.6 \times 10^5$ | 0.075 |
| GFP-C-polyOEGMA (D = 26 nm) | 2.4 | 27 | $1.3 \times 10^7$ | 0.016 |
| GFP-C-polyOEGMA (D = 42 nm) | 2.6 | 24 | $1.3 \times 10^7$ | 0.018 |
| GFP-C-polyOEGMA (D = 80 nm) | 2.2 | 18 | $1.5 \times 10^7$ | 0.015 |

Example 15

Tumor Inoculation Using GFP Conjugate

Female nude mice (Balb/c nu/nu) with an average body weight of about 20 g were purchased from CCIF. Animals were housed in appropriate isolated caging with sterile rodent food and acidified water ad libitum and a 12-h light/dark cycle. The tumor leg xenograft was established from a human squamous cell carcinoma (FaDu) tumor cell line. FaDu cells were cultured as a monolayer in tissue culture flasks containing minimal essential medium (MEM) supplemented with Earle's salts, L-glutamine, 10% heat-inactivated FBS, 100 U/ml penicillin, 100 µg/ml streptomycin and 0.25 µg/ml amphotericin B (Gibco, Carlsbad, Calif.). They were grown at 37° C. with 5% $CO_2$ in air. The right lower leg of each mouse was implanted s.c. with $1\times10^6$ cells of FaDu in 50 µl of PBS. Tumors was allowed to grow to 150 $mm^3$ in diameter before starting treatment, typically about 14 days after inoculation. Tumor volume was determined using the equation: volume=$(width)^2$*length*0.52 by measuring the size by clipper. Mice were carefully monitored for general well-being, weight, and tumor volume. All animal experiments were performed in accordance with the Duke University Institutional Animal Care and Use Committee.

Biodistribution was determined. After tumor growth to a size of 150 $mm^3$, the mice were randomly divided into groups of 5 mice each. The groups were received intravenous bolus injections of a given amount of PBS solution of $^{125}I$ labeled GFP and GFP-C-poly(OEGMA) conjugate, respectively. Each animal was given intravenously the dose of 0.3 µg GFP (component) with a trace of $^{125}I$ (~5 µCi). The injection volume of the sample solution was calculated by (Body weight/9)*51. Mice were euthanized with decapitation under Anesthesia overdosing Halothane or pentobarbital (250 mg/kg, i.p.) at given time points after i.v. administration. Tumor, blood, thyroid, heart, lung, liver, spleen, kidney, muscle and skin were collected for counting on γcounter.

FIG. 35 shows that tumor accumulation was significantly improved after poly(OEGMA) conjugation of GFP.

Example 16

In Vitro Stability Study

The in vitro stability of 125I labeled Mb and Mb-N-pOEGMA will be determined by incubating 20 µL of each with 180 µL each of fresh mouse serum, resulting in a final Mb concentration of 10 µM. Samples will be collected from the mixture at 0 s, 40 s, 15 min, 30 min, 1 h, 2 h, 4 h, 8 h, 24 h, 48 h, 72 h and immediately stored at −20° C. Each sample will be run on an SDS-PAGE gel (15 µL), which will be further dried and then exposed to a storage phosphor screen for autoradiography analysis using densimetry. The degradation will be calculated by dividing the radioactivity for each sample by the radioactivity at 0 s.

Example 17

In Vivo Stability Study

Mice will be randomly divided into groups and each group will have 4 mice. These groups will be received intravenous bolus injections of a given amount of PBS solution of 125I labeled Mb and Mb-N-pOEGMA conjugates, respectively. The injection solution amount is calculated according to an empirical formula: (Wmouse body/9)*51. 20 µL of blood will be collected at various time points from tail vein. The serum will be separated from whole blood by centrifugation. Each sample will be run on SDS-PAGE gel, which will be dried and then exposed to a storage phosphor screen for autoradiography analysis using densimetry. The degradation will be calculated by dividing the radioactivity for each sample by the radioactivity at 0 s.

Example 18

Immunogenicity Study

Mice will be randomly divided into groups and each group will have 4 mice. These groups will be received intravenous bolus injections of a given amount of PBS solution of Mb and Mb-N-pOEGMA conjugates, respectively. Mb-N-pOEGMA and Mb (10 µg equivalent) in 200 µL of PBS or with Freund's adjuvant system will be intravenously injected into Balb/c mice and/or nude mice bearing mouse breast carcinoma xenograft (4T1). The animals will be reimmunized in a similar manner at day 49 post primary immunization. Blood samples will be taken at days 14, 21, and 28 after primary immunization, and 10 days after secondary immunization (day 59). Serum will be obtained by centrifugation of blood samples. Samples will be stored at −70° C. before antibody analysis. Quantitation of Mb and Mb-N-pOEGMA specific antibodies in serum collected from immunized mice will be performed by an ELISA. Briefly, Mb or Mb-N-pOEGMA (100 µL, 0.1 µg/mL) will be added to 96-well microtiter plates and allowed to stand for 2 h at room temperature. The plates will be washed with PBS, and then a solution of BSA in PBS (100 µL) will be added and allowed to stand at room temperature for 2 h. The plates will be washed with PBS, and the mouse serum (serially diluted with PBS) will be added (50 µL) and allowed to stand overnight at 4° C. The plates will be washed with PBS and a secondary antibody of goat anti-mouse IgG labeled with horseradish peroxidase (0.01 µg, 50 µL) will be added and incubated at 37° C. for 2 h. The plates will be washed with PBS and a substrate solution (50 µL) of 3,3',5,5'-tetramethylbenzidine [0.1 mg in 10 mL of sodium acetate (0.1 M, pH 6.0)] will be added. Optical density readings will be recorded at 450 nm. The plates will be developed in the dark for 30 min. Sulfuric acid (1.0 M, 50 µL) will be added to quench the reaction. A simple linear regression analysis of an immunoglobulin titration-generated reference curve will be used to extrapolate the amount of specific antibodies contained in the test sample. The Student's t-test will be used to calculate confidence level values at each time point. The data will be reported as the mean value of the four mice in each group the standard error of the mean.

Example 19

RAFT Polymerization 200 mg of protein macroRAFT agent will be dissolved in 5 ml of phosphate buffer (pH=6). A monomer solution (4 ml, 0.67 M, 2.4 mmol) in phosphate buffer is added slowly to the solution. The final concentration ratios will be as follows: [monomer]0:[protein-macroRAFT]0:[Initiator]0=1800.0: 1.0:4.7.

Following the sealing of the vials with rubber septa, the polymerization solutions will be deoxygenated for 30 mins in an ice bath. A deoxygenated solution of the initiator (4,4'-azobis[2-9-imidazolin-2-ethyl)propane] dihydrochloride, 1 ml, 6.35 mM, in phosphate buffer (pH=6)) is introduced into the reaction mixture at 0° C. using a syringe. The solution is further deoxygenated at 0° C. for 30 min and then placed in a water bath at 25° C. Aliquots (1 ml) are taken at predetermined time intervals and quenched via rapid cooling and exposure to oxygen.

Example 20

Construction of GLP-intein-ELP Constructs

Two different GLP peptides will by synthesized (Table 1). Wild type GLP is expected to show the highest activity but low stability due to the existence of a DPPIV cleavage site. A mutated GLP will also be made having lower (~4 fold) activity than wild type GLP (Green et al., J of Mol Endocrin, 31(3): 529-540), but being resistant to DPPIV cleavage. To prevent any errors from post-translational de-methylation, a protective peptide, encoding for an entrokinase cleavage site will be added to the N-terminal of all peptides. Following expression and entrokinase cleavage we expect an intact N-terminal GLP. GLP gene constructs (wild type and mutant) will be chemically synthesized (IDT DNA technologies) and ligated to an inducible pET32 expression vector containing an intein sequence followed by elastin-like polypeptide (ELP) tag for non-chromatographic purification. Constructs will be sequenced to verify correctness of insert.

TABLE 3

Peptide sequences of WT and mutant GLP. Underlined sequences represent entrokinase protective peptide, sequences underlined represent DPPIV cleavage. site.

| Gene | Sequence |
| --- | --- |
| Wild type GLP | MSDDDDKHAEGTFTSDVSSVLEGQAAKEFIAWLVKGR |
| DPPIV resistant GLP | MSDDDDKHVEGTFTSDVSSVLEGQAAKEFIAWLVKGR |

Example 21

Expression and Purification of GLP-intein-ELP Fusion Proteins

Each gene will be expressed in *E. coli* from a pET32 expression plasmid transformed into BL21(DE3) cells under control of the strong T7 promoter by adding IPTG after 6 h growth and including expression for an additional 18 h (long IPTG induction). The expressed GLP-intein-ELP fusions will be purified by Inverse Transition Cycling (ITC), a facile non-chromatographic method developed by the PI to purify ELPs and their fusion proteins. (Lim, et al., Biomacromolecules, 8: 1417-1424; Trabbic-Carlson, K., Protein Science 13: 3274-3284). Previous studies in our group have shown that 5 rounds of ITC provides highly pure ELP. (McHale et al., Tissue Engineering, 11: 1768-1779) GLP-intein-ELP yield per liter will be measured by UV-vis spectrophotometry using the known extinction coefficients of the ELPs (Pace et al., Protein Science 4: 2411-2423). Entrokinase cleavage will be performed using entrokinase light chain (NEB) by incubation over-night at room temperature. Following cleavage, another round of ITC will separate GLP-intein-ELP containing fraction from protease and cleaved protective enzyme.

Example 23

(SA3): Cleavage of GLP from Intein-ELP and PEGylation of GLP to form PEGylated GLP as a Control GLP will be cleaved from intein-ELP by adding mercaptoethane sulfonate or DTT in PBS to a buffer solution of GLP-intein-ELP fusion protein and incubating the mixture solution for 24 h at room temperature. (Ge et al., J. Am. Chem. Soc., 127: 11228-11229). Following cleavage, one round of ITC will separate GLP from intein-ELP and unreacted GLP-intein-ELP. GLP will further be purified by chromatography (AKTA) or spin ultrafiltration. PEGylated GLP will be prepared by adding excess monomethoxy poly(ethylene glycol) succinimidyl propionate (mPEG-SPA) in DMF into a buffer solution of GLP. (Youn et al., Biochem. Pharmacol, 73: 84-93). The reaction will be allowed to continue for 1 h at room temperature. PEGylated GLP will be purified by chromatography (AKTA) and characterized by SDS-PAGE, HPLC and MALDI-MS. This PEGylated GLP will be used as a control.

Example 24

(SA4): Synthesis of a Cysteine-functionalized ATRP Initiator

2-Amino-N-[2-(2-bromo-2-methyl-propionylamino)-ethyl]-3-mercapto-propionamide (ABMP) will be synthesized by using a synthetic route as shown in FIG. 36. Briefly, N-(tert-butoxycarbonyl)-S-trityl-L- and N-(2-aminoethyl)-2-bromo-2-methylpropanamide.HCl will be dissolved in a mixture of anhydrous dichloromethane and anhydrous N,N-dimethylformamide. To this ice-cooled solution is added PyBOP and anhydrous triethylamine. The reaction is allowed to warm to room temperature and stirring is continued for 22 h. The reaction mixture will be concentrated to dryness under reduced pressure and purified by silica gel flash column chromatography. Deprotection is accomplished by stirring a mixture of the protected amide, TFA, $H_2O$ and triisopropylsilane at room temperature for 15 minutes. The reaction mixture is concentrated to dryness under reduced pressure and the residue is partitioned between $H_2O$ and dichloromethane. The aqueous phase is washed with dichloromethane and concentrated to dryness (lyophilization) to give the desired product. The purified product will be characterized by NMR and mass spectrometry.

Example 25

(SA5): Cleavage of GLP from Intein-ELP with ABMP to Form GLP-Br, and Protection of the Thiol Group with Maleimide As shown in FIG. 37, GLP will be cleaved from intein-ELP by adding ABMP to form GLP-Br. After one round of ITC to separate GLP-Br from intein-ELP and unreacted GLP-intein-ELP, GLP-Br will further be purified by chromatography (AKTA) or spin ultrafiltration. The thiol group will be protected by adding maleimide into GLP-Br solution to form GLP-M-Br. The reaction will be allowed to continue for 1 h at room temperature. GLP-M-Br will be purified by chromatography (AKTA) or spin ultrafiltration. The protection of the thiol will be determined by Ellman's assay. GLP-Br and GLP-M-Br will be characterized by MALDI-MS and ESI-MS. To determine the C-terminal modification, a lysyl endoproteinase, Lys-C, digestion will be performed. Briefly, the enzyme will be added to a buffer solution of GLP-Br or GLP-M-Br. The reaction will be allowed to incubate for 1 h at 37° C. The reaction solution will be analyzed by LC-MS/MS.

Example 26

(SA6): In Situ Growth of poly(oligo(ethylene glycol) methacrylate) (poly(OEGMA) or poly(carboxybetaine methacrylate) (poly(CBMA)) Conjugates at the C-terminus of GLP by ATRP A solution composed of 2 mg CuCl, 4 mg $CuCl_2$ and 16 mg 1,1,4,7,10,10-Hexamethyltriethylenetetramine (HMTETA), 500 mg OEGMA or CBMA, 1 mL PBS will be deoxygenated and transferred into a deoxygenated GLP-M-Br solution in PBS. The polymerization will be allowed to proceed for a given time under argon and then exposed to air. The polymerization solutions will be directly analyzed by HPLC and SDS-PAGE. After purification with AKTA, GLP-C-poly (OEGMA)/poly(CBMA) will be further characterized by HPLC, SDS-PAGE, DLS and NMR.

Example 27

(SA7): Radiolabelling of GLP-C-polyOEGMA, PEGylated GLP and GLP

Iodination of GLPs with $^{125}$I will be conducted with Pierce IODO-Gen Pre-coated tube and purified by passing through desalting dextran column (Pierce). In the labeling reaction, iodous ions ($I^+$) are produced by oxidation of iodide ($I^-$) by Pierce Iodination Reagent and undergo electrophilic attack at the ortho-ring position of tyrosines of Mb at neutral pH values. The radioactivity will be counted by gamma counter (LKB-Wallac, Turku, Finland) and the labeling efficiency will be calculated by the equation: % Efficiency=(Radioactivity of collected conjugate/Total loaded radioactivity)*100. The concentration of iodinated GLPs will be measured by UV-Vis spectroscopy.

Example 28

(SA8): In Vivo Pharmacokinetics of GLP-C-polyOEGMA, PEGylated GLP and GLP in Mice Coujugating GLP-1 with polyOEGMA will be expected to dramatically improve pharmacokinetics of GLP-1 through a stealth effect. Briefly, Balb/c mice will be randomly divided into groups and each group will have 4 mice. These groups will be received intravenous bolus injections of a given amount of PBS solution of $^{125}$I labeled GLPs, respectively. Each animal will be given intravenously the dose of 0.3 µg GLP (component) with a trace of $^{125}$I (~5 µCi). Blood samples (20 µL) will be collected from the tail vein of the mice at preset time points after injection. The whole blood sample will be analyzed by gamma counting. The blood concentration will be calculated by normalizing the percent injected dose per gram (% ID/g) at each time point by the 40 s time point. The blood concentration time-course will be analyzed with a standard two-compartment pharmacokinetic modal to approximate both distribution and elimination of the samples.

Example 29

(SA9): In Vitro Stability of GLP-C-polyOEGMA, PEGylated GLP and GLP

Although DPPIV acts rapidly to deactivate GLP-1 by cleavage of the His-Ala dipeptide from the N-terminus, the long polyOEGMA chain may protect the N terminus from cleavage by hindering DPPIV binding. We will examine the effect of DPPIV on GLPs by incubating peptides with recombinant, purified DPPIV as well as with blood serum for varying periods of time. As GLP-1 activity is most sensitive to changes at the N-terminus. (Knudsen, J. Med. Chem., 47: 4128-4134). ELISA will be performed with mouse monoclonal antibodies raised against the N-terminus of GLPs (Santa Cruz Biotechnology Inc.) to ensure that the N-terminal region of GLPs is active. Wild type GLP-1 (positive control), as well as both wild type and DPPIV resistant GLPs will be immobilized to a 96-well, high binding plate, and incubated with GLP-1 specific antibody. Detection of antibody binding will be performed incubation with anti-mouse antibodies conjugated to biotin and colorimetric analysis of oxidized tetramethylbenzidine by avidin conjugated-HRP (eBiosciences). Degradation half-life ($t_{1/2}$) values will be obtained from time versus concentration curves.

Example 30

(SA10): In Vivo Stability of GLP-C-polyOEGMA, PEGylated GLP and GLP

Briefly, Balb/c mice will be randomly divided into groups and each group will have 4 mice. These groups will be received intravenous bolus injections of a given amount of PBS solution of GLPs, respectively. Blood samples (20 µL) will be collected from the tail vein of the mice at preset time points after injection. Blood serum will be separated and be immobilized to a 96-well, high binding plate, and incubated with GLP-1 specific antibody. Detection of antibody binding will be performed incubation with anti-mouse antibodies conjugated to biotin and colorimetric analysis of oxidized tetramethylbenzidine by avidin conjugated-HRP (eBiosciences). Degradation half-life ($t_{1/2}$) values will be obtained from time versus concentration curves.

Example 31

(SA11): In Vitro Bioactivity of GLP-C-polyOEGMA, PEGylated GLP and GLP

The ability of GLPs to activate the GLP-1 receptor (GLP-1-R) in vitro will be assessed using baby hamster kidney (BHK) cells expressing rat GLP-1-R and receptor activation by measurements of intra-cellular cyclic-AMP concentration as a function of proteolytic enzyme concentration. Drucker et al., Lancet, 368: 1696-1705). BHK cells stably transfected with rat GLP-1R will be grown in medium containing 0.05 mg/ml Gentamicin. For analysis, BHK-GLP-1R cells will be allowed to reach 70-80% confluence in 24-well plates in the absence of G418 at 37° C. Cells will be incubated with varying concentration of GLPs, as well as wild type unmodified GLP-1 as control. Intracellular cAMP concentration will be measured calorimetrically by competitive binding of cAMP bound to Alakaline-phosphatase and cAMP in the sample and consequent oxidation of Alkaline-phosphatase sensitive substrate (Parameter™).

Example 32

(SA12): In Vivo Bioactivity of GLP-C-polyOEGMA, PEGylated GLP and GLP

In vivo biological potency of GLPs will be assessed by oral glucose tolerance testing (OGTT) [7]. Briefly, db/db mice will be randomly divided into groups for GLPs and each group will have 4 mice. Diabetic mice fasted for 18 h will be i.v. administered with PBS, GLPs at predetermined times (−30, −120, −240, and −360 min) prior to orally administering glucose to mice. 20 uL of blood will be collected from tail veins at 0, 15, 30, 45, 60, 90, 120, and 180 min, and blood glucose levels (BGL) will be determined using a one-touch blood glucose meter (ACCU-CHEK Sensor, Roche Diagnostics Corp., Indianapolis, Ind.). Three factors will be used to evaluate the glucose-stabilizing activity: (1) maximum blood glucose level ($BGL_{max}$); (2) required time to lower BGL below 5.5 mmol/L ($t_{BGL<5.5\ mmol/L}$), and (3) total hypoglycemic degree (THGD). THGD will be calculated as follows: $[(AUC_{PBS}-AUC_{GLP})/AUC_{PBs}]*100$.

Example 33

In Situ ATRP from DNA and siRNA

DNA and siRNA will be selectively modified at the 5' or 3' end with ATRP initiators to DNA and siRNA macroinitiators (DNA and SiRNA-Br). After purification, a deoxygenated solution of 1 mL PBS, 1.05 mmol poly(ethylene glycol) methyl ether methacrylate (OEGMA) (MW=475, Sigma-Aldrich), 0.02 mmol CuCl, 0.044 mmol $CuCl_2$, and 0.087 mmol 1,1,4,7,10,10-hexamethyltriethylenetetramine (HMTETA) will be transferred into a deoxygenated DNA/siRNA-Br solution in PBS. The polymerization will be allowed to proceed for a given time under argon and then exposed to air. The polymerization mixture will be further purified with HPLC (AKTA, GE Life Science) using a size exclusion column.

The DNA-polymer conjugates and siRNA conjugates are expected to show improved pharmacological properties including increased in vivo half-life and greater in vivo biodistribution to a cell, tissue, organ or disease site.

Various features and advantages of the invention are set forth in the following claims.

What is claimed is:

1. A method of making polypeptide-polymer conjugates, having one or more altered pharmacological properties, from a plurality of polypeptides having N-termini and C-termini, the method comprising:
   a) contacting the plurality of polypeptides with an initiator agent under conditions that permit attachment of the initiator agent to at least one of the N-terminus and the C-terminus; and
   b) incubating the plurality of polypeptides with a monomer under conditions that permit polymerization to occur from the initiator agent to form a plurality of polypeptide-polymer conjugates, such that at least about 10% of the polypeptides have a conjugated polymer initiated from at least one of the N-terminus and the C-terminus,
   wherein the plurality of polypeptide-polymer conjugates have an altered pharmacological property selected from the group consisting of (i) an in vivo half-life that is at least 25% greater compared with the in vivo half life of the plurality of polypeptides lacking polymer conjugates; (ii) an in vivo biodistribution to a tissue, organ or disease site that is at least 25% greater than the in vivo biodistribution of the plurality of polypeptides lacking polymer conjugates; and (iii) combinations thereof;
   and wherein the polymerization comprises a polymerization reaction selected from the group consisting of atom transfer radical polymerization (ATRP), reversible addition-fragmentation chain transfer (RAFT), ring opening metathesis polymerization (ROMP), and combinations thereof.

2. The method of claim 1, wherein at least about 10% of the polypeptide-polymer conjugates have a single polymer conjugated per polypeptide.

3. The method of claim 1, wherein the plurality of polypeptides comprise one or more peptides or protein therapeutic agents selected from the group consisting of an inteferon, insulin, monoclonal antibody, blood factor, colony stimulating factor, growth hormone, interleukin, growth factor, therapeutic vaccine, calcitonin, tumor necrosis factors (TNF), enzyme, and conbinations thereof.

4. The method of claim 1, wherein the monomer comprises at least one of an acrylate, methacylate, acrylamide, and methacrylamide.

5. The method of claim 1, wherein the polymer has side chains comprising moieties selected from oligoethylene glycol, betaine, carboxybetaine, sulfobetaine, phosphorylcholine or a combination thereof.

6. The method of claim 1, wherein at least one of the polypeptides has a thioester at the C-terminus to which the initiator agent attaches in step (a).

7. The method of claim 6, wherein the thioester is introduced at the C-terminus by attaching an intein sequence comprising the thioester to the polypeptide and detaching the intein sequence without the thioester from the protein or peptide.

8. The method of claim 1, wherein at least one of the polypeptides has an aldehyde group at the N-terminus to which the initiator agent attaches in step (a).

9. The method of claim 8, wherein the aldehyde group is introduced at the N-terminus by a transamination reaction.

10. The method of claim 1, wherein the initiator agent is a compound selected from the group consisting of [N-(2-aminoethyl)-2-bromo-2-methylpropanamide, 2-bromo-N-(2-(2-hydrazinylacetamido)ethyl)-2-methylpropanamide], a cysteine-functionalized ATRP initiator and a RAFT agent.

11. The method of claim 1, wherein the plurality of polypeptides and monomer are incubated with a catalyst in step (b).

12. The method of claim 1, wherein the plurality of polypeptide-polymer conjugates have an in vivo half-life that is at least 80% greater than the in vivo half-life of the plurality of polypeptides lacking polymer conjugates.

* * * * *

SEQUENCE LISTING

<160> NUMBER OF SEQ ID NOS: 22

<210> SEQ ID NO 1
<211> LENGTH: 16
<212> TYPE: PRT
<213> ORGANISM: Equus ferus

<400> SEQUENCE: 1

Gly Leu Ser Asp Gly Glu Trp Gln Gln Val Leu Asn Val Trp Gly Lys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 2

Lys Leu Ala Ala Ala Leu Gly Ser Gly Ser Gly Met Arg Met
1               5                   10

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
catgcgtatg tgcatcacgg gagat                                          25

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
ggcctgagtt cagaccggtg a                                              21

<210> SEQ ID NO 5
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 5

Met Ser Asp Asp Asp Lys His Ala Glu Gly Thr Phe Thr Ser Asp
1               5                   10                  15

Val Ser Ser Val Leu Glu Gly Gln Ala Ala Lys Glu Phe Ile Ala Trp
            20                  25                  30

Leu Val Lys Gly Arg
        35

<210> SEQ ID NO 6
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 6

Met Ser Asp Asp Asp Lys His Val Glu Gly Thr Phe Thr Ser Asp
1               5                   10                  15

Val Ser Ser Val Leu Glu Gly Gln Ala Ala Lys Glu Phe Ile Ala Trp
            20                  25                  30

Leu Val Lys Gly Arg
        35

<210> SEQ ID NO 7
<211> LENGTH: 12
<212> TYPE: PRT
<213> ORGANISM: Equus ferus

<400> SEQUENCE: 7

Ala Leu Glu Leu Phe Arg Asn Asp Ile Ala Ala Lys
1               5                   10

<210> SEQ ID NO 8
<211> LENGTH: 15
<212> TYPE: PRT
<213> ORGANISM: Equus ferus

<400> SEQUENCE: 8

His Pro Gly Asp Phe Gly Ala Asp Ala Gln Gly Ala Met Thr Lys
1               5                   10                  15

<210> SEQ ID NO 9
<211> LENGTH: 11
<212> TYPE: PRT
<213> ORGANISM: Equus ferus

<400> SEQUENCE: 9

Leu Phe Thr Gly His Pro Glu Thr Leu Glu Lys
1               5                   10

<210> SEQ ID NO 10
<211> LENGTH: 14
<212> TYPE: PRT
<213> ORGANISM: Equus ferus

<400> SEQUENCE: 10

Leu Phe Thr Gly His Pro Glu Thr Leu Glu Lys Phe Asp Lys
1               5                   10

<210> SEQ ID NO 11
<211> LENGTH: 15
<212> TYPE: PRT
<213> ORGANISM: Equus ferus

<400> SEQUENCE: 11

```
Val Glu Ala Asp Ile Ala Gly His Gly Gln Glu Val Leu Ile Arg
1               5                   10                  15

<210> SEQ ID NO 12
<211> LENGTH: 8
<212> TYPE: PRT
<213> ORGANISM: Equus ferus

<400> SEQUENCE: 12

Tyr Lys Glu Leu Gly Phe Gln Gly
1               5

<210> SEQ ID NO 13
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 13

Ala Ser Lys Gly Glu Glu Leu Phe Thr Gly Val Val Pro Ile Leu Val
1               5                   10                  15

Glu Leu Asp Gly Asp Val Asn Gly His Lys
            20                  25

<210> SEQ ID NO 14
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 14

Gly Glu Glu Leu Phe Thr Gly Val Val Pro Ile Leu Val Glu Leu Asp
1               5                   10                  15

Gly Asp Val Asn Gly His Lys
            20

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Phe Ser Val Ser Gly Glu Gly Glu Gly Asp Ala Thr Tyr Gly Lys
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 16

Phe Ser Val Ser Gly Glu Gly Glu Gly Asp Ala Thr Tyr Gly Lys Leu
1               5                   10                  15

Thr Leu Lys

<210> SEQ ID NO 17
<211> LENGTH: 16
<212> TYPE: PRT
<213> ORGANISM: Artificial Sequence
<220> FEATURE:
```

<223> OTHER INFORMATION: Synthetic Peptide

<400> SEQUENCE: 17

Ser Ala Met Pro Glu Gly Tyr Val Gln Glu Arg Thr Ile Phe Phe Lys
1               5                   10                  15

<210> SEQ ID NO 18
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 18

Ser Ala Met Pro Glu Gly Tyr Val Gln Glu Arg Thr Ile Phe Phe Lys
1               5                   10                  15

Asp Asp Gly Asn Tyr Lys
            20

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 19

Phe Glu Gly Asp Thr Leu Val Asn Arg Ile Glu Leu Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 20

Gly Ile Asp Phe Lys Glu Asp Gly Asn Ile Leu Gly His Lys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 21

Leu Glu Tyr Asn Tyr Asn Ser His Asn Val Tyr Ile Met Ala Asp Lys
1               5                   10                  15

<210> SEQ ID NO 22
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 22

Thr Arg His Asn Ile Glu Asp Gly Ser Val Gln Leu Ala Asp His Tyr
1               5                   10                  15

```
Gln Gln Asn Thr Pro Ile Gly Asp Gly Pro Val Leu Leu Pro Asp Asn
                20                  25                  30

His Tyr Leu Ser Thr Gln Ser Ala Leu Ser Lys
            35                  40
```